Figure 1:
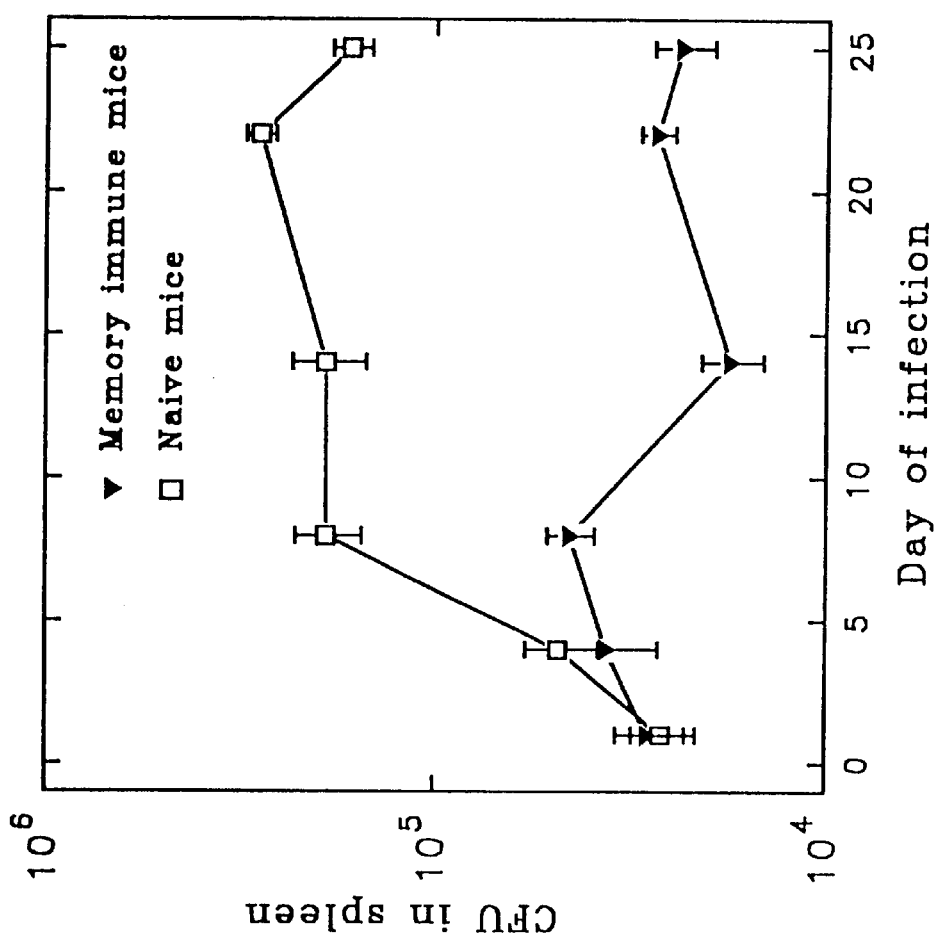
Figure 2:
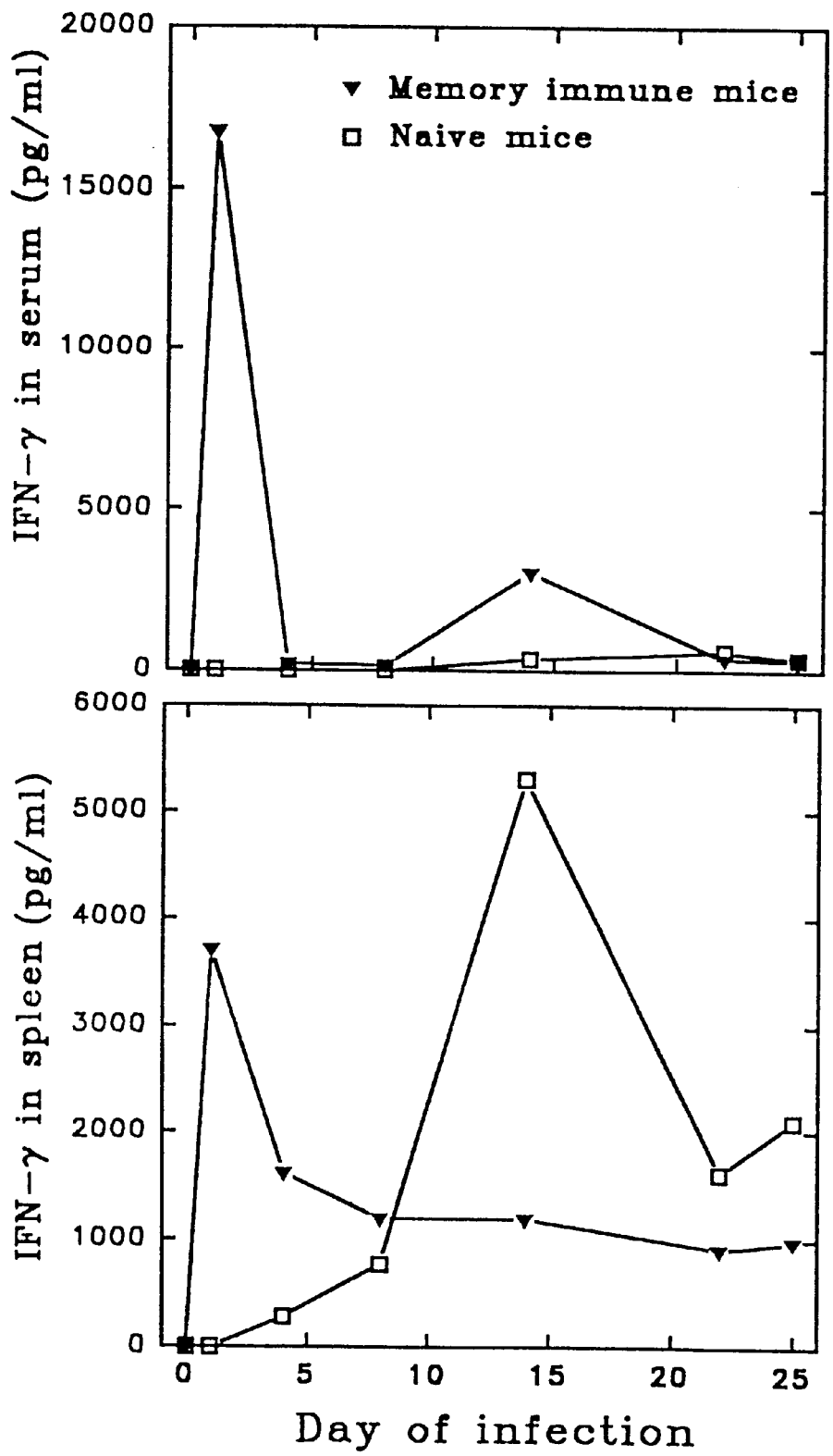
Figure 3:
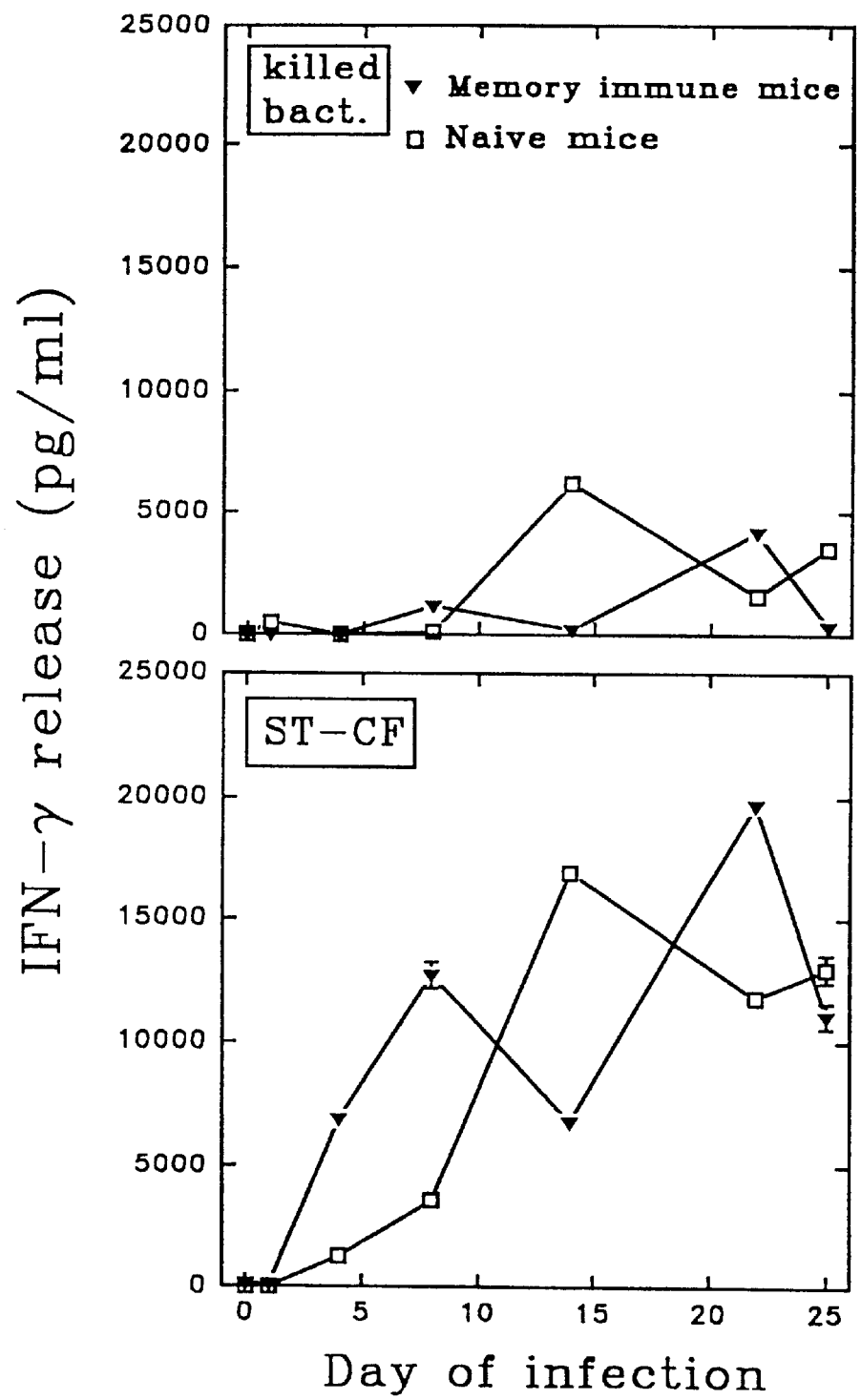
Figure 4:
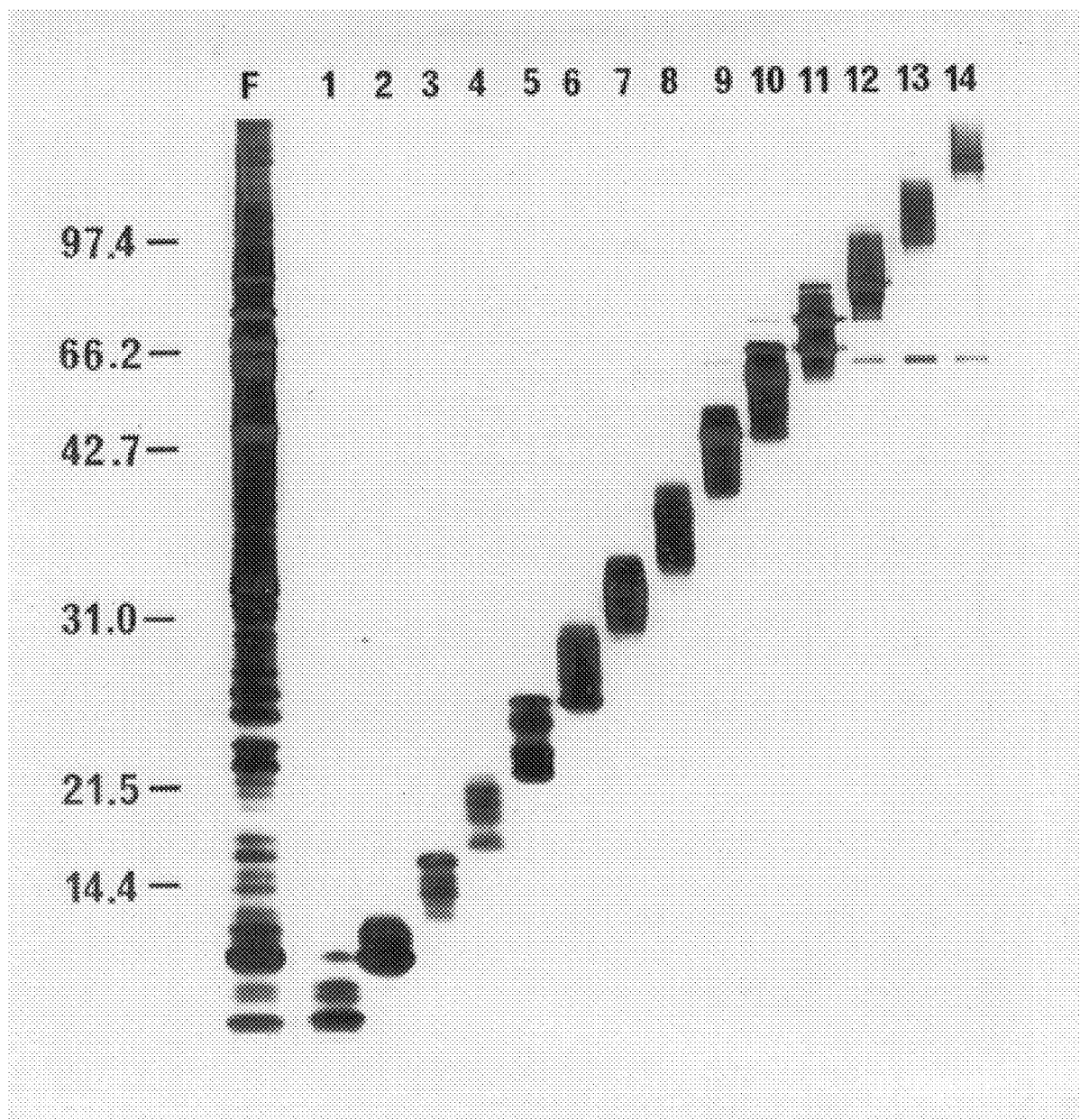

United States Patent [19]
Andersen et al.

[11] Patent Number: 5,955,077
[45] Date of Patent: Sep. 21, 1999

[54] TUBERCULOSIS VACCINE

[75] Inventors: Peter Andersen; Åse Bengaard Andersen, both of Bronshoj; Kaare Haslov, Soborg; Anne Lund Sorensen, Bronshoj, all of Denmark

[73] Assignee: Statens Seruminstitut, Copenhagen, Denmark

[21] Appl. No.: 08/465,640

[22] Filed: Jun. 5, 1995

Related U.S. Application Data

[63] Continuation-in-part of application No. 08/123,182, Sep. 20, 1993, abandoned, and application No. PCT/DK94/00273, Jul. 1, 1994.

[51] Int. Cl.$^6$ .......................... A61K 39/00; A61K 39/04; C12P 21/06; C07K 1/00
[52] U.S. Cl. ..................................... 424/184.1; 424/185.1; 424/190.1; 424/234.1; 424/248.1; 435/69.3; 435/71.1; 435/325; 530/300; 530/327; 530/344; 530/350; 530/412; 536/23.7
[58] Field of Search ..................................... 530/350, 300, 530/327, 344, 412; 540/12; 424/184.1, 185.1, 190.1, 234.1, 248.1; 435/69.3, 71.1, 325; 536/23.7

[56] References Cited

U.S. PATENT DOCUMENTS

| | | |
|---|---|---|
| 4,891,315 | 1/1990 | Watson et al. . |
| 4,952,395 | 8/1990 | Shinnick et al. . |
| 4,976,958 | 12/1990 | Shinnick et al. . |
| 5,026,546 | 6/1991 | Hilgers et al. . |
| 5,330,754 | 7/1994 | Kapoor et al. . |
| 5,559,011 | 9/1996 | Kapoor et al. . |

OTHER PUBLICATIONS

Boswell et al Computational Molecular Biology, Oxford University Press, pp. 161–178, 1988.
Andersen et al, *T–Cell Proliferative Response to Antigens Secreted by Mycobacterium tuberculosis*, Infection and Immunity, vol. 59, No. 4, pp. 1558–1563, Apr. 1991.
Andersen et al, *Proteins Released from Mycobacterium tuberculosis during Growth*, Infection and Immunity, vol. 59, No. 6, pp. 1905–1910, Jun. 1991.
Andersen et al, *Specificity of a Protective Memory Immune Response against Mycobacterium tuberculosis*, Infection and Immunity, vol. 61, No. 3, pp. 844–851, Mar. 1993.
Andersen and Heron, *Simultaneous electroelution of whole SDS–polyacrylamide gels for the direct cellular analysis of complex protein mixtures*, Journal of Immunological Methods, vol. 161, pp. 29–39, 1993.
Flesch and Kaufmann, *Mycobacterial Growth Inhibition by Interferon–y–Activated Bone Marrow Macrophages and Differential . . . tuberculosis*, The Journal of Immunology, vol. 138, No. 12, pp. 4408–4413, Jun. 15, 1987.
Lefford and McGregor, *Immunological Memory in Tuberculosis*, Cellular Immunology, vol. 14, pp. 417–428, 1974.
Orme, *Characteristics and Specificity of Acquired Immunologic Memory to Mycobacterium tuberculosis Infection* The Journal of Immunology, vol. 140, No. 10, pp. 3589–3593, May 15, 1988.

G.A.W. Rock, *The Role of Activated Macrophages in protection and immunopathology in Tuberculosis*, Research in Microbiology vol. 141, No. 2, Feb. 1990, pp. 253–256.
Sanger, Nicklen, and Coulson, *DNA Sequencing with Chain–Terminating Inhibitors*, Proc. Natl. Acad. Sci USA, vol. 74, No. 12, pp. 5463–5467, Dec. 1977.
Young, Bloom, Grosskinsky, Ivanyi, Thomas and Davis, *Dissection of Myobacterium Tuberculosis antigens Using recombinant DNA*, Proc. Natl. Acad. Sci. USA, vol. 82, pp. 2583–2587, May 1985.
Andersen, Askgaard, Gottschau, Bennedsen, Nagai and Heron, *Identification of Immunodominant Antigens during Infection with Mycobacterium tuberculosis*, Scand. J. Immunol., vol. 36, pp. 823–831, 1992.
Huygen, Abramowicz, Vandenbussche, Jacobs, De Bruyn, Kentos, Drowart, Van Vooren, and Goldman, *Spleen Cell Cytokine Secretion in Mycobacterium bovis BCG–Infected Mice*, Infection And Immunity, vol. 60, No. 7, pp. 2880–2886, Jul. 1992.
Abou–Zeid, Ratliff, Wiker, Harboe, Bennedsen and Rook, *Characterization of Fibronectin–Binding Antigens Released by Mycobacterium tuberculosis and Mycobacterium bovis BCG*, Infection and Immunity, vol. 56, No. 12, pp. 3046–3051, Dec. 1988.
Borremans, De Wit, Volckaert, Ooms, De Bruyn, Huygen, Van Vooren, Stelandre, Verhofstadt, Content, *Cloning, Sequence Determination, and Expression of a 32–Kilodalton–Protein Gene of Mycobacterium tuberculosis*, Infection and Immunity, vol. 57, No. 10, pp. 3123–3130, Oct. 1989.
Barnes et al (Journal of Immunology vol. 148 Mar. 15, 1992 pp. 1835–1840).
Kaufman (Microbiological Sciences 4 (11) Nov. 1987 pp. 324–328).
Lazar et al (Molecular & Cellular Bio. Mar. 1988 pp. 1247–1252).
Burgess et al (J. of Cell Biology vol. III Nov. 1990 pp. 2129–2138).
Salgaller et al (Cancer Immuno. Imnuother. (1994) vol. 39 pp. 105–116).

*Primary Examiner*—Anthony C. Caputa
*Assistant Examiner*—Mark Navarro
*Attorney, Agent, or Firm*—Iver P. Cooper

[57] ABSTRACT

The invention relates to novel secreted antigens from mycobacteria capable of evoking early (within 4 days) immunological responses from T-helper cells in the form of gamma-interferon release in memory immune animals after rechallenge infection with mycobacteria of the tuberculosis complex. The antigens are present in short term filtrates (ST-CF) from cultured mycobacteria belonging to the tuberculosis complex. One of these antigens, a polypeptide with an apparent molecular weight of 6 kDa, has been identified, and the DNA encoding the polypeptide has been cloned and sequenced. The antigens of the invention are believed useful especially in vaccines, but also in diagnostic compositions, especially for diagnosing infection with virulent mycobacteria. Also disclosed are nucleic acid fragments encoding the antigens as well as methods of immunizing animals/humans and methods of diagnosing tuberculosis.

30 Claims, 18 Drawing Sheets

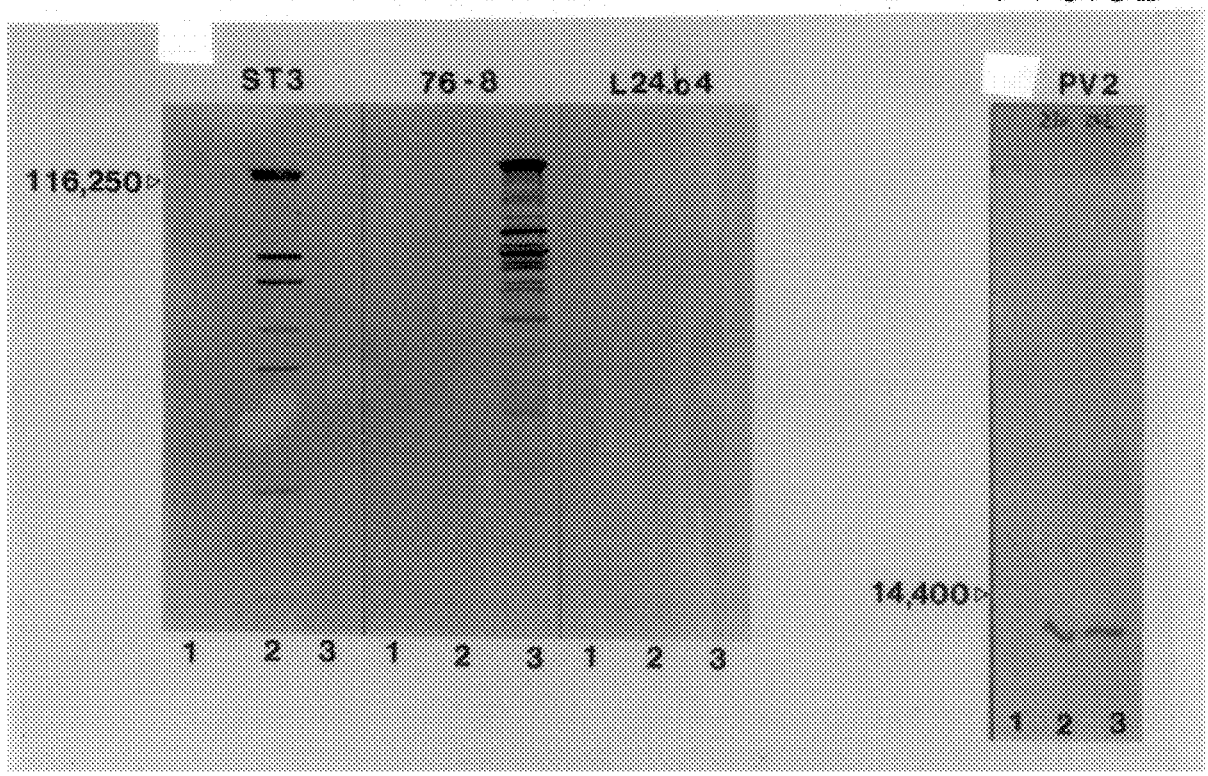

```
   1 GAATTCCAAA ACATGACAGA GCAGCAGTGG AATTTCGCGG GTATCGAGGC
  51 CGCGGCAAGC GCAATCCAGG GAAATGTTCAC GTCCATTCAT TCCCTCCTTG
 101 ACGAGGGGAA GCAGTCCCTG ACCAAGCTCG CAGCGGCCTG GGGCGGTAGC
 151 GGTTCGGAGG CGTACCAGGG TGTCCAGCAA AAATGGGACG CCACGGCTAC
 201 CGAGCTGAAC AACGCGCTGC AGAACCTGGC GCGGACGATC AGCGAAGCCG
 251 GTCAGGCAAT GGCTTCGACC GAAGGCAACG TCACTGGGAT GTTCGCATAG
 301 GGCAACGCCG AGTTCGCGTA GAATAGCGAA ACACGGGATC GGGCGAGTTC
 351 GACCTTCCGT CGGTCTCGCC CTTTCTCGTG TTTATACGTT TGAGCGCACT
 401 CTGAGAGGTT GTCATGGCGG CCGACTACGA CAAGCTCTTC CGGCCGCACG
 451 AAGGTATGGA AGCTCCGGAC GATATGGCAG CGCACGCGTT CTTCGACCCC
 501 AGTGCTTCGT TTCCGCCGGC GCCCGCATCG GCAAACCTAC CGAAGCCCAA
 551 CGGCCAGACT CCGCCCCCGA CGTCCGACGA CCTGTCGGAG CGGTTCGTGT
 601 CGGCCCCGGC CGCCACCCCC CCACCCCCAC CTCCGCCTCC GCCAACTCCG
 651 ATGCGATCGC GCAGGAGAGC CGCCCTCGCC GGAACCGGCC GCATCTAAAC
 701 CACCCACACC CCCCATGCCC ATCGCCGGAC CCGAACCGGC CCCACCCAAA
 751 CCACCCACAC CCCCCATGCC CATCGCCGGA CCCGAACCGG CCCCACCCAA
 801 ACCACCCACA CTCCGATGCC CATCGCCGGA CCTGCACCCC ACCCAACGAA
 851 TCCCAGTTGG CGCCCCCCAG ACCACCGACA CCACAAACGC CAACCGGAGC
 901 GCCGCAGCAA CCGGAATCAC CGGTGCCCCA CGTACCCTCG CACGGGCCAC
 951 ATCAACCCCG GTGCACCGCA CCAGCACCGC CCTGGGCAAA GATGCCAATC
1001 GGCGAACCCC CGCCCGCCCG TCCAGACCGT CTGCGTCCCC GGCCGAACCA
1051 CCGACCCGGC CTGCCCCCCA ACACTCCCGA CGTGCGCGCC GGGGTCACCG
1101 CTATCGCACA GACACCGAAC GAAACGTCGG GAAGGTAGCA ACTGGTCCAT
1151 CCATCCAGGC GCGGCTGCGG GCAGAGGAAG CATCCGGCGC GCAGCTCGCC
1201 CCCGGAACGG AGCCCTCGCC AGCGCCGTTG GGCCAACCGA GATCGTATCT
1251 GGCTCCGCCC ACCCGCCCCG CGCCGACAGA ACCTCCCCCC AGCCCCTCGC
1301 CGCAGCGCAA CTCCGGTCGG CGTGCCGAGC GACGCGTCCA CCCCGATTTA
1351 GCCGCCCAAC ATGCCGCGGC GCAACCTGAT TCAATTACGG CCGCAACCAC
1401 TGGCGGTCGT CGCCGCAAGC GTGCAGCGCC GGATCTCGAC GsGrmAACAG
1451 AAATCCTTAA GCCGGCGCGA AGGGGCCGCA AGGTGAAGAA GGTGAAGCCC
1501 CAGAAACCGA AGGCCACGAA GCCGCCCAAA GTGGTGTCGC AGCGCGGCTG
1551 GCGACATTGG GTGCATGCGT TGACGCGAAT CAACCTGGGC CTGTCACCCG
1601 ACGAGAAGTA CGAGCTGGAC CTGCACGCTC GAGTCCGCCG CAATCCCCGC
1651 GGGTCGTATC AGATCGCCGT CGTCGGTCTC AAAGGTGGGG CTGGCAAAAC
1701 CACGCTGACA GCAGCGTTGG GGTCGACGTT GGCTCAGGTG CGGGCCGACC
1751 GGATCC
```

Fig. 10B

* * * * * * *
MetThrGluGlnTrpAsnPheAlaGlyIleGluAlaAlaAlaSerAlaIleGlnGly –

AsnValThrSerIleHisSerLeuLeuAspGluGlyLysGlnSerLeuThrLysLeuAla –

AlaAlaTrpGlyGlySerGlySerGluAlaTyrGlnGlyValGlnLysTrpAspAla –

ThrAlaThrGluLeuAsnAsnAlaLeuGlnAsnLeuAlaArgThrIleSerGluAlaGly –

GlnAlaMetAlaSerThrGluGlyAsnValThrGlyMetPheAla.

Fig. 10C

TUBERCULOSIS VACCINE

This application is a continuation-in-part of a) U.S. Ser. No. 08/123,182 filed Sep. 20, 1993 now abandoned and of b) PCT/DK94/00273 filed Jul. 1, 1994.

The present invention relates to a novel vaccine for immunizing an animal, including a human being, against tuberculosis. The invention further relates to methods and means for the diagnosis of tuberculosis.

BACKGROUND

Human tuberculosis caused by *Mycobacterium tuberculosis* is a severe global health problem responsible for approximately 3 million deaths annually (NIH report). The worldwide incidence of new tuberculosis cases has been progressively falling for the last decade but the recent years has markedly changed this trend due to the advent of AIDS and the appearance of multidrug resistant strains of *M. tuberculosis* (Rieder).

The only vaccine presently available is BCG, a vaccine which efficacy remains a matter of controversy. BCG generally induces a high level of acquired resistance in animal models of tuberculosis (Smith), but several human trials in developing countries have failed to demonstrate significant protection (Fine).

This makes the development of a new and improved vaccine against tuberculosis an urgent matter which has been given a very high priority by the WHO (WHO BULL). Many attempts to define protective mycobacterial substances have been made, and from 1950 to 1970 several investigators reported an increased resistance after experimental vaccination. However, the demonstration of a specific long-term protective immune response with the potency of BCG has not yet been achieved by administration of soluble proteins or cell wall fragments. Immunity to *M. tuberculosis* is characterized by three basic features; i) Living bacilli efficiently induces a protective immune response in contrast to killed preparations (Orme); ii) Specifically sensitized T lymphocytes mediate this protection (Mackaness, Orme); iii) The most important mediator molecule seems to be interferon gamma (INF-γ) (Rook, Flesh).

Proteins secreted by *M. tuberculosis* when grown in culture have been demonstrated to function as stimulators of specific cellular immune responses in mice, and it has been suggested that possible antigens useful in new vaccines against tuberculosis should be sought among such proteins. However, no immune dominant antigen has been isolated or identified.

DESCRIPTION OF THE INVENTION

It is an object of the present invention to provide a vaccine for immunizing an animal, including a human being against tuberculosis caused by mycobacteria belonging to the tuberculosis-complex.

It is demonstrated herein that secreted antigens administered together with an appropriate adjuvant induces specific long-lived Th-1 cells capable of protecting against a subsequent challenge with virulent *M. tuberculosis*. Importantly, it has surprisingly been found that a vaccine based on soluble polypeptides has the same protective potency as live BCG, especially polypeptides as described below.

Consequently, an aspect of the invention is a vaccine for immunizing an animal, including a human being, against tuberculosis caused by mycobacteria belonging to the tuberculosis-complex, comprising as the effective component at least one at least partially purified polypeptide, which is released from metabolizing mycobacteria and present in short-term filtrates from such mycobacteria grown as shaken cultures for 7 days, and has a molecular weight in the range from about 3 to about 16 kDa or in the range from about 20 to about 40 kDa as determined by analysis by SDS-PAGE and silver staining, and induces a release of IFN-γ from reactivated memory T-lymphocytes withdrawn from a C57Bl/6j mouse within 4 days after the mouse has been rechallenge infected with mycobacteria belonging to the tuberculosis complex, the induction performed by the addition of the polypeptide to a suspension comprising about 200.000 reactivated memory T-cells per ml, the addition of the polypeptide resulting in a concentration of 1 μg polypeptide per ml suspension, and the release of IFN-γ being assessable by determination of IFN-γ in supernatant harvested 2 days after the addition of the polypeptide to the suspension, or an analogue and/or subsequence of the polypeptide, said analogue and/or subsequence being immunologically equivalent to the polypeptide with respect to the ability of evoking a protective immune response against tuberculosis or with respect to the ability to elicit a delayed type hypersensitivity reaction, said polypeptide optionally being coupled to a pharmaceutically acceptable carrier or vehicle.

The tuberculosis-complex has its usual meaning, i.e. the complex of mycobacteria causing tuberculosis which are *Mycobacterium tuberculosis*, *Mycobacterium bovis*, and *Mycobacterium africanum*.

In the present context the term "metabolizing mycobacteria" means live mycobacteria that are multiplying logarithmically and releasing polypeptides into the culture medium.

By the term "polypeptide" is herein meant both short peptides with a length of at least two amino acid residues and at most 10 amino acid residues, oligopeptides (11–100 amino acid residues), and longer peptides (the usual interpretation of "polypeptide", i.e. more than 100 amino acid residues in length) as well as proteins (the functional entity comprising at least one peptide, oligopeptide, or polypeptide which may be chemically modified by being glycosylated, by being lipidated, or by comprising prosthetic groups). The definition of polypeptides also comprises native forms of peptides/proteins in mycobacteria as well as recombinant proteins or peptides in any type of expression vectors transforming any kind of host, and also chemically synthesized peptides.

By the terms "analogue" and "subsequence" when used in connection with polypeptides is meant any polypeptide having the same immunological characteristics as the polypeptides of the invention described above with respect to the ability to confer increased resistance to infections with bacteria belonging to the tuberculosis complex. Thus, included is also a polypeptide from different sources, such as other bacteria or even from eukaryotic cells.

The terms "analogue" and "subsequence" with regard to a polypeptide of the invention are also used in the present context to indicate a protein or polypeptide of a similar amino acid composition or sequence as the characteristic amino acid sequence shown in SEQ ID NO: 2, allowing for minor variations which do not have an adverse effect on the ligand binding properties and/or biological function and/or immunogenicity, or which may give interesting and useful novel binding properties or biological functions and immunogenicities etc. The analogous polypeptide or protein may be derived from other microorganisms, cells, or animals and the analogue may also be derived through the use of recombinant DNA techniques as described below.

Furthermore, in the present context the term "immunologically equivalent" means that the analogue or subsequence of the polypeptide is functionally equivalent to the polypeptide with respect to the ability of evoking a protective immune response against tuberculosis and/or eliciting a diagnostically significant immune response (e.g. a Dth reaction).

The term "protective immune response" has its usual meaning, i.e. that the immune response evoked by the polypeptide in question protects the person immunized from contracting tuberculosis, or that the immune response evoked by the polypeptide at least confers a substantially increased resistance to infections with mycobacteria belonging to the tuberculosis complex.

The ability of the polypeptide to evoke a protective immune response may be assessed by measuring in an experimental animal, e.g. a mouse or a guinea pig, the reduction in mycobacterial counts from the spleen, lung or other organ homogenates isolated from the experimental animal which have received a challenge infection with a virulent strain of *Mycobacterium tuberculosis* after previously having been immunized with the polypeptide, as compared to the mycobacterial counts in a control group of experimental animals infected with the same virulent strain of *Mycobacterium tuberculosis*, which experimental animals have not previously been immunized against tuberculosis. The comparison of the mycobacterial counts may also be carried out with mycobacterial counts from a group of experimental animals receiving a challenge infection with the same virulent strain after having been immunized with *Mycobacterium bovis* BCG.

The mycobacterial counts in homogenates from the experimental animals immunized with a polypeptide according to the present invention must at the most be 5 times the counts in the mice or guinea pigs immunized with *Mycobacterium bovis* BCG, such as at the most 3 times the counts, and preferably at the most 2 times the counts.

"Immunologically equivalent" may also mean that the analogue or subsequence is functionally equivalent with the polypeptide with respect to eliciting a delayed type hypersensitivity (Dth) reaction to an extent of at least 45% of the Dth reaction elicited by the polypeptide under the same conditions, such as at least 65%, and preferably 85%, measured as the diameter of the Dth reaction.

The inventors of the present invention have realised that the polypeptides as defined above are of great importance in evoking a protective immune response against tuberculosis because they induce a release of IFN-γ from reactivated T-lymphocytes from an animal or a human being shortly after the animal or human being have been reinfected.

This has been confirmed by measuring the IFN-γ release induced from reactivated T lymphocytes withdrawn from a C57Bl/6j mouse within 4 days after the mouse have been rechallenge infected with mycobacteria belonging to the tuberculosis-complex. This is due to the fact that when an immune host mounts a protective immune response, the specific T-cells responsible for the early recognition of the infected macrophage, stimulates a powerful bactericidal activity through their production of IFN-γ (Rook, G.A.W. 1990., Flesch, I. et al. 1987).

It is contemplated that because the polypeptides stimulate the T lymphocyte immune response shortly after the onset of the infection they are important in the control of the mycobacteria causing the infection before the mycobacteria have succeeded in multiplying up to the number of bacteria that would have resulted in fulminant infection.

Hence, the polypeptides described herein as components in the vaccine are also in their own right an important part of the invention as are the nucleotide fragments encoding the polypeptides of the invention.

The polypeptides of interest are within the two main molecular ranges as defined above, but may be within about 4 to about 14 kDa, such as about 6 to about 10 kDa.

In a preferred embodiment the polypeptide has a molecular weight in the range of about 5 kDa to about 6 kDa, in the range of about 6 kDa to about 7 kDa or in the range of about 7 kDa to about 8 kDa.

The polypeptides may also lie within another molecular interval which is about 22 to about 38 kDa, or about 20 to about 32 kDa, such as about 22 kDa to about 30 kDa, or even about 24 kDa to about 28 kDa, some other polypeptides may be in the interval of about 35 to about 40 kDa, such as about 36 to about 39 kDa, or even about 36 to about 38 kDa.

In a more preferred embodiment the molecular weight may be within about 25 kDa to about 27 kDa or about 37 to about 38 kDa.

As described in the examples, three clones of *E. coli* expressing low molecular weight mycobacterial polypeptides from ST-CF have been produced and isolated; all of these proteins are suspected of being involved in the early T-cell responses described above. Thus, according to the invention the polypeptides produced by the lysogenic *E. coli* strain designated AA226 which has been deposited 28 June 1993 with the collection of Deutsche Sammlung von Mikroorganismen und Zellkulturen GmbH (DSM) under the accession number DSM 8377, and/or produced by the lysogenic *E. coli* strain designated AA227 which has been deposited Jun. 28, 1993 with the collection of Deutsche Sammlung von Mikroorganismen und Zellkulturen GmbH (DSM) under the accession number DSM 8378, and/or produced by the lysogenic *E. coli* strain designated AA242 which has been deposited 28 June 1993 with the collection of Deutsche Sammlung von Mikroorganismen und Zellkulturen GmbH (DSM) under the accession number DSM 8379 all depositions in accordance with the provisions of the Budapest Treaty, are regarded as interesting aspects of the invention.

It has been demonstrated that a low molecular weight protein expressed by the strain AA227 exhibits the immunological profile described above, i.e. has the ability to induce INFγ release from reactivated memory T-lymphocytes withdrawn from C57Bl/6j mice 4 days after rechallenge infection with mycobacteria; this protein is thus an especially preferred aspect of the invention.

The protein expressed by this strain binds specifically to a monoclonal antibody designated HYB76-8. Thus, an interesting aspect of the invention is also a polypeptide reacting in a western blot assay with a monoclonal antibody, HYB76-8, said antibody being produced by the hybridoma cell line designated HYB 76-8 0,5/br C8 0,25/br B3 which has been deposited Jun. 30, 1993 with the collection of Deutsche Sammlung von Mikroorganismen und Zellkulturen GmbH (DSM) under the accession number DSM ACC2134 in accordance with the provisions of the Budapest Treaty.

However, it has been shown by the inventors that the above described immunological profile is not exhibited by any protein expressed by the strain AA226, although this strain expresses another low molecular weight antigen from ST-CF. Therefore, it seems that not all low molecular antigens in ST-CF are directly responsible for or involved in the above-discussed immunological properties of ST-CF, whereas the HYB76-8 reactive antigen must be regarded as one major candidate for the major immunogenic component in a tuberculosis vaccine comprised of single antigens. As discussed below, the mycobacterial antigen expressed by AA226 might possibly have an effect as an "adjuvant" in ST-CF, i.e. the protein is not responsible for the elicitation of the immune response, but has an effect which facilitates the elicitation of efficient immune responses.

In a preferred embodiment of the invention the amino acid sequence of the polypeptide comprises an amino acid sequence homologous to the amino acid shown in SEQ ID NO: 2 (cf. also FIG. 10) in the N-terminal part of the sequence or homologous to the amino acid sequence of a analogue and/or subsequence of the amino acid sequence of SEQ ID NO: 2.

The term "homologous" is used here to illustrate the degree of identity between the amino acid sequence of a given polypeptide and the amino acid sequence shown in SEQ ID NO: 2 The amino acid sequence to be compared with the amino acid sequence shown in SEQ ID NO: 2 may be deduced from a DNA sequence, e.g. obtained by hybridization as defined below, or may be obtained by conventional amino acid sequencing methods. The degree of homology is preferably determined on the amino acid sequence of a mature polypeptide, i.e. without taking any leader sequence into consideration. It is preferred that the degree of homology is at least 80%, such as at least 90%, preferably at least 95% or even 98% with the amino acid sequence shown in SEQ ID NO: 2.

Each of the polypeptides may be characterized by specific amino acid and nucleic acid sequences. It will be understood that such sequences include analogues and variants produced by recombinant methods wherein such nucleic acid and polypeptide sequences have been modified by substitution, insertion, addition and/or deletion of one or more nucleotides in said nucleic acid sequences to cause the substitution, insertion, addition or deletion of one or more amino acid residues in the recombinant polypeptide. When the term DNA is used in the following, it should be understood that for the number of purposes where DNA can be substituted with RNA, the term DNA should be read to include RNA embodiments which will be apparent for the man skilled in the art. For the purposes of hybridization, PNA may be used instead of DNA, as PNA has been shown to exhibit a very dynamic hybridization profile (PNA is described in Nielsen P E et al., 1991, Science 254: 1497–1500).

In order to evoke a protective immune response, a polypeptide must be at least 12 amino acids long, preferably at least 15 amino acids, such as 20 amino acids.

The nucleotide sequence encoding the above-defined polypeptide may be a nucleotide which 1) is the DNA sequence shown in SEQ ID NO: 1 (shown in FIG. 10) or an analogue and/or subsequence of said sequence which hybridizes with the DNA sequence shown in SEQ ID NO: 1 (or a DNA fragment complementary thereto) or a specific part thereof, preferably under stringent hybridization conditions (as defined in the art that is 5–10° C. under the melting point $T_m$, cf. Sambrook et al, 1989, pages 11.45–11.49), and/or 2) encodes a polypeptide, the amino acid sequence of which is at least 80% homologous with the amino acid sequence shown in SEQ ID NO: 2, and/or 3) constitutes an effective subsequence of said DNA sequence.

The terms "analogue" or "subsequence" when used in connection with the DNA fragments of the invention are intended to indicate a nucleotide sequence which encodes a polypeptide exhibiting identical or substantially identical immunological properties to a polypeptide encoded by the DNA fragment of the invention shown in SEQ ID NO: 1.

It is well known that the same amino acid may be encoded by various codons, the codon usage being related, inter alia, to the preference of the organisms in question expressing the nucleotide sequence. Thus, at least one nucleotide or codon of a DNA fragment of the invention may be exchanged by others which, when expressed, result in a polypeptide identical or substantially identical to the polypeptide encoded by the DNA fragment in question.

Therefore, the terms "analogue" or "subsequence" are used in the present context to indicate a DNA fragment or a DNA sequence of a similar nucleotide composition or sequence as the DNA sequence encoding the amino acid sequence constituting ESAT6 (also denoted "the 6 kDa antigen" or "the HYB76-8 reactive antigen") described herein, allowing for minor variations which do not have an adverse effect on the ligand binding properties and/or biological function and/or immunogenicity as compared to ESAT6, or which give interesting and useful novel binding properties or biological functions and immunogenicities etc. of the analogue and/or subsequence. The analogous DNA fragment or DNA sequence may be derived from a bacterium, an animal, or a human or may be partially or completely of synthetic origin as described above. The analogue and/or subsequence may also be derived through the use of recombinant DNA techniques.

Furthermore, the terms "analogue" and "subsequence" are intended to allow for variations in the sequence such as substitution, insertion (including introns), addition, deletion and rearrangement of one or more nucleotides, which variations do not have any substantial effect on the polypeptide encoded by a DNA fragment or a subsequence thereof. The term "substitution" is intended to mean the replacement of one or more nucleotides in the full nucleotide sequence with one or more different nucleotides, "addition" is understood to mean the addition of one or more nucleotides at either end of the full nucleotide sequence, "insertion" is intended to mean the introduction of one or more nucleotides within the full nucleotide sequence, "deletion" is intended to indicate that one or more nucleotides have been deleted from the full nucleotide sequence whether at either end of the sequence or at any suitable point within it, and "rearrangement" is intended to mean that two or more nucleotide residues have been exchanged with each other.

A nucleotide subsequence as discussed above refers to an "effective subsequence" which means that it encodes a peptide which is immunologically functional with respect to the ability of evoking a protective immune response against tuberculosis or of eliciting a Dth reaction. The subsequence may be the result of a truncation at either end of the DNA sequence and/or of the removal of one or more nucleotides or nucleotide sequences within DNA sequence.

The polypeptide is, as described above, released from the metabolizing mycobacteria, and may therefore be a polypeptide which is translated from a gene in the genome of the mycobacteria. However, the polypeptide released may also be a degradation product of a larger polypeptide which is catabolized or disintegrated within the mycobacteria whereupon only the products of the catabolization or disintegration are released from the mycobacteria. Therefore, the nucleotide sequence encoding the polypeptide may be part of a larger nucleotide sequence encoding the larger polypeptide present within the living bacteria only. It is in this connection understood that shaken cultures grown for 7 days as described above only represent an insignificantly number of lysed mycobacteria which of course will not secrete any polypeptides but result in release of all (also purely intracellular) polypeptides into the filtrate.

A vaccine according to the invention is preferably one which is capable of evoking a substantial and specific acquired immune resistance in a mouse or guinea pig against tuberculosis caused by mycobacteria belonging to the tuberculosis-complex, which acquired immune resistance corresponds to at least 20%. of the protective immune resistance elicited by *Mycobacterium bovis* BCG, as assessed by the observed reduction in mycobacterial counts from spleen, lung or other organ homogenates isolated from the mouse or guinea pig receiving a challenge infection with a virulent strain of *M. tuberculosis*, as described above.

The preferred acquired immune resistance corresponds to at least 50% of the protective immune response elicited by *M. bovis* BCG, such as at least 60%, or even more preferred to at least 80% of the protective immune response elicited by *M. bovis* BCG, such as at least 90%.

When compared to the immune response elicited by *M. bovis* BCG it is possible in a preferred aspect of the present invention that the vaccine confers to the person vaccinated an acquired immune resistance corresponding to at least 100% of the protective immune response elicited by *M. bovis* BCG, such as at least 110%.

Preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10–95% of active ingredient, preferably 25–70%.

The proteins may be formulated into the vaccine as neutral or salt forms. Pharmaceutically acceptable salts include acid addition salts (formed with the free amino groups of the peptide) and which are formed with inorganic acids such as, for example, hydrochloric or phosphoric acids, or such organic acids as acetic oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 $\mu$g to 1000 $\mu$g, such as in the range from about 1 $\mu$g to 300 $\mu$g, and especially in the range from about 10 $\mu$g to 50 $\mu$g. Suitable regimes for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

Some of the polypeptides of the vaccine are sufficiently immunogenic in a vaccine, but for some of the others the immune response will be enhanced if the vaccine further comprises an adjuvant substance.

Various methods of achieving adjuvant effect for the vaccine include use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° to 101° C. for 30 second to 2 minute periods respectively. Aggregation by reactivating with pepsin treated (Fab) antibodies to albumin, mixture with bacterial cells such as *C. parvum* or endotoxins or lipopoly-saccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. According to the invention DDA (dimethyldioctadecylammonium bromide) is an interesting candidate for an adjuvant, but also Freund's complete and incomplete adjuvants as well as QuilA and RIBI are interesting possibilities.

Other possibilities involve the use of immune modulating substances such as lymphokines (e.g. IFN-$\gamma$, IL-2 and IL-12) or synthetic IFN-$\gamma$ inducers such as poly I:C in combination with the above-mentioned adjuvants. As discussed in example 3, it is contemplated that such mixtures of antigen and adjuvant will lead to superior vaccine formulations.

In many instances, it will be necessary to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain the desired levels of protective immunity. The course of the immunization may be followed by in vitro proliferation assays of PBL (peripheral blood lymphocytes) co-cultured with ESAT6 or ST-CF, and especially by measuring the levels of IFN-γ released form the primed lymphocytes. The assays may be performed using conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

As described above a measurement of the effect of the polypeptides in the vaccine may be to assess the IFN-γ released from memory T-lymphocytes. The stronger immune response the more IFN-γ will be released, accordingly, a vaccine according to the invention comprises a polypeptide capable of releasing from the memory T-lymphocytes at least 1500 pg/ml, such as 2000 pg/ml, preferably 3000 pg/ml IFN-γ.

Due to genetic variation different individuals may react with immune responses of varying strength to the same polypeptide. Therefore, the vaccine according to the invention may comprise several different polypeptides in order to increase the immune response. The vaccine may comprise two or more polypeptides, where all of the polypeptides are as defined above, or some but not all of the peptides may be derived from a bacterium belonging to the *M. tuberculosis* complex. In the latter example the polypeptides not necessarily fulfilling the criteria set forth above for polypeptides may either act due to their own immunogenicity or merely act as adjuvants. Examples of such interesting polypeptides are MPB64, MPT64, the ST-3 reactive polypeptide, the PV-2 reactive polypeptide, and MPB59, but any other substance which can be isolated from mycobacteria are possible candidates.

The vaccine may comprise 3–20 different polypeptides, such as 3–10 different polypeptides.

One reason for admixing the polypeptides of the invention with an adjuvant is to effectively activate a cellular immune response. However, this effect can also be achieved in other ways, for instance by expressing the effective antigen in a vaccine in a non-pathogenic microorganism. A well-known example of such a microorganism is *Mycobacterium bovis* BCG.

Therefore, another important aspect of the present invention is an improvement of the BCG vaccine presently available, which is a vaccine for immunizing an animal, including a human being, against tuberculosis caused by mycobacteria belonging to the tuberculosis-complex, comprising as the effective component a microorganism, wherein one or more copies of a DNA sequence encoding a polypeptide as defined above or an analogue and/or subsequence thereof has been incorporated into the genome of the microorganism in a manner allowing the microorganism to express and secrete the polypeptide.

In the present context the term "genome" refers to the chromosome of the microorganisms as well as extrachromosomally DNA or RNA, such as plasmids.

The assessment of the capability of the vaccine with respect to evoking a protective immune response being as defined above, as well as the assessment of the effect of the vaccine as compared to conventional BCG vaccine.

The microorganism in the vaccine may be a bacterium such as bacteria selected from the group consisting of the genera Mycobacterium, Salmonella, Pseudomonas and Eschericia.

In a preferred embodiment the microorganism is *Mycobacterium bovis* BCG, and in a more preferred embodiment it is *Mycobacterium bovis* BCG strain: Danish 1331, which is the *Mycobacterium bovis* strain Copenhagen from the Copenhagen BCG Laboratory, Statens Seruminstitut, Denmark.

The incorporation of one or more copies of a DNA sequence encoding the polypeptide according to the invention in a mycobacterium from a *M. bovis* BCG strain will enhance the immunogenic effect of the BCG strain especially with respect to the long-term immune response as described above. The incorporation of more than one copy of the DNA sequence is contemplated to enhance the immune response even more, consequently an aspect of the invention is a vaccine wherein at least 2 copies of a DNA sequence encoding a polypeptide is incorporated in the genome of the microorganism, such as at least 5 copies. The copies of DNA sequences may either be identical encoding identical polypeptides or be variants of the same DNA sequence encoding identical or homologues of a polypeptide, or in another embodiment be different DNA sequences encoding different polypeptides where at least one of the polypeptides is according to the present invention.

The DNA sequence used in such an embodiment of the invention may be a DNA sequence which 1) is identical to the DNA sequence shown in SEQ ID NO: 1 or an analogue and/or subsequence which hybridizes with the DNA sequence shown in SEQ ID NO: 1 (or a DNA sequence complementary thereto) or a specific part thereof, preferably under stringent hybridization conditions and/or
2) encodes a peptide, the amino acid sequence of which is at least 80% homologous with the amino acid sequence shown in SEQ ID NO: 2, and/or
3) constitutes an effective subsequence of said DNA sequence, the definitions of analogue and subsequence being as defined above.

The DNA sequence is according to the invention preferably one that encodes a peptide the amino acid sequence of which is at least 90% homologous with the amino acid sequence shown in SEQ ID NO: 2 or with a subsequence thereof, or encodes the peptide with the amino acid sequence shown in SEQ ID NO: 2, or encodes a subsequence thereof.

As discussed above, the elicitation of cell-mediated responses to infection can be obtained by employing an adjuvant or by using live vaccines. However, recent research have revealed a new an exciting possibility, wherein a DNA fragment cloned in a vector which is non-replicative in eukaryotic cells is introduced into an animal (including a human being) by e.g. intramuscular injection or percutaneous administration. The DNA is taken up by e.g. muscle cells and the gene of interest is expressed by a promoter which is functioning in eukaryotes, e.g. a viral promoter, and the gene product thereafter stimulates the immune system. These newly discovered methods are reviewed in Ulmer et al., 1993, which hereby is included by reference.

Therefore, also a part of the invention is a vaccine comprising a nucleic acid fragment according to the invention, the vaccine effecting in vivo expression of antigens by an animal, including a human being, to whom the vaccine has been administered, the amount of expressed antigens being effective to confer substantially increased resistance to infections with mycobacteria of the tuberculosis complex in an animal, including a human being. Also, methods of immunizing animals against tuberculosis by administering the vaccine to the animals are parts of the invention.

The efficacy of such a "DNA vaccine" can possibly be enhanced by administering the gene encoding the expression product together with a DNA fragment encoding a polypeptide which has the capability of modulating an immune response. For instance, a gene encoding lymphokine precursors or lymphokines (e.g. IFN-γ, IL-2, or IL-12) could be administered together with the gene encoding the immunogenic protein, either by administering two separate DNA fragments or by administering both DNA fragments included in the same vector.

In both immunodiagnostics and vaccine preparation, it is often possible and practical to prepare antigens from segments of a known immunogenic protein or polypeptide. Certain epitopic regions may be used to produce responses similar to those produced by the entire antigenic polypeptide. Potential antigenic or immunogenic regions may be identified by any of a number of approaches, e.g., Jameson-Wolf or Kyte-Doolittle antigenicity analyses or Hopp and Woods (1981) hydrophobicity analysis (see, e.g., Jameson and Wolf, 1988; Kyte and Doolittle, 1982; or U.S. Pat. No. 4,554,101). Hydrophobicity analysis assigns average hydrophilicity values to each amino acid residue from these values average hydrophilicities can be calculated and regions of greatest hydrophilicity determined. Using one or more of these methods, regions of predicted antigenicity may be derived from the amino acid sequence assigned to the polypeptides of the invention.

Therefore, yet another aspect of the present invention is the polypeptide as defined above, especially one which comprises an epitope for a T-helper cell.

Examples of such polypeptides are those produced by the deposited E. coli strains described above.

Furthermore, the invention relates to a nucleotide fragment comprising a nucleotide sequence encoding a polypeptide as defined above, such as a nucleotide sequence encoding any one of the polypeptides produced by the deposited E. coli strains described above, especially the nucleotide fragment which comprises the DNA sequence of SEQ ID NO: 1.

Yet another aspect of the invention is a composition for diagnosing tuberculosis, comprising a polypeptide as defined above, especially the polypeptides produced by the deposited E. coli strains described above, such as the polypeptide encoded by a nucleotide fragment which comprises the DNA sequence of SEQ ID NO: 1 or a part thereof, or the composition comprising a nucleotide sequence as defined above. The diagnostic composition should, when prepared for in vivo use, further comprise a pharmaceutically acceptable carrier or vehicle. Thus, the vehicle may be a diluent, a suspending agent or other similar agents, and typically the vehicle will be a physiological buffer such as e.g. PBS.

Methods of determining the presence of mycobacterial antibodies or components of mycobacteria in samples or in animals are also parts of the invention, as is a method of determining the presence of antibodies directed against mycobacteria belonging to the tuberculosis complex in an animal, including a human being, or in a sample, comprising administering a polypeptide of the invention to the animal or incubating the sample with the polypeptide of the invention, and detecting the presence of bound antibody resulting from the administration or incubation. Likewise, a method of determining the presence of a mycobacterial antigen in an animal, including a human being, or in a sample, comprising administering an antibody of the invention to the animal or incubating the sample with the antibody, and detecting the presence of bound antigen resulting from the administration or incubation, forms part of the invention. Finally a method of determining the presence of mycobacterial nucleic acids in an animal, including a human being, or in a sample, comprising administering a nucleic acid fragment of the invention to the animal or incubating the sample with the nucleic acid fragment of the invention or a nucleic acid fragment complementary thereto, and detecting the presence of hybridized nucleic acids resulting from the incubation (by using the hybridization assays which are well-known in the art), is also included in the invention. Such a method of diagnosing tuberculosis might involve the use of a composition comprising at least a part of a nucleotide sequence as defined above and detecting the presence of nucleotide sequences in a sample from the animal or human being to be tested which hybridize with the nucleotide fragment (or a complementary fragment) by the use of PCR technique.

Preferred immunoassays are contemplated as including various types of enzyme linked immunoassays (ELISAS), immunoblot techniques, and the like, known in the art. However, it will be readily appreciated that utility is not limited to such assays, and useful embodiments include RIAs and other non-enzyme linked antibody binding assays or procedures.

It is contemplated that several assays for the presence of mycobacteria or for TB may be developed using any of the polypeptides of the invention, the corresponding nucleic acid fragments encoding the protein, functionally similar proteins and their epitopes, or by detection of other appropriate nucleic acids. Reactive epitopes representing portions of the polypeptide sequences could be utilized in an analogous manner.

Finally, diagnostic kits for the diagnosis of on-going or previous TB infection forms part of the invention. The diagnostic kits of the invention comprises an antibody, a nucleic acid, or a polypeptide according to the invention in combination with a means for detecting the interaction with the relevant substance reacting with these substances of the invention; the choice of these detection means is discussed below with reference to DNA fragments, but it will be understood that the same considerations apply for polypeptides and monoclonal antibodies of the invention.

In both the diagnostic methods, compositions, and kits the antibodies, nucleic acids or polypeptides according to the invention may optionally be coupled to solid or semi-solid carriers, as is well-known in the art.

In clinical diagnostic embodiments, nucleic acid segments of the present invention may be used in combination with an appropriate means, such as a tag or a label, to determine hybridization with DNA of a pathogenic organism. Typical methods of detection might utilize, for example, radioactive species, enzyme-active or other marker ligands such as avidin/biotin, which are detectable directly or indirectly. In preferred diagnostic embodiments, one will likely desire to employ an enzyme tag such as alkaline phosphatase or peroxidase rather than radioactive or other reagents that may have undesirable environmental effects. Enzyme tags, for example, often utilize calorimetric indicator substrates that are readily detectable spectrophotometrically, many in the visible wavelength range. Luminescent substrates could also be used for increased sensitivity.

Hybridizable DNA segments may include any of a number of segments of the disclosed DNA. For example, relatively short segments including 12 or so base pairs may be employed, or, more preferably when probes are desired, longer segments including 20, 30 or 40 base pairs, depending on the particular applications desired. Shorter segments are preferred as primers in such applications as PCR, while some of the longer segments are generally preferable for blot hybridizations. It should be pointed out, however, that while sequences disclosed for the DNA segments of the present invention are defined by SEQ ID NO: 1 a certain amount of variation or base substitution would be expected, e.g., as may be found in mutants or strain variants, but which do not significantly affect hybridization characteristics. Such variations, including base modifications occurring naturally or otherwise, are, as mentioned above intended to be included within the scope of the present invention.

As explained below, at least one of the polypeptides of the invention is present in virulent mycobacteria, but absent from most non-virulent mycobacteria. It is expected that this will also be the case for other polypeptides of the invention. The gene encoding the polypeptide has also been shown to exhibit the same species distribution, and therefore the diagnostic embodiments discussed above using the nucleotide fragments of the invention are important in methods for detecting the presence of virulent mycobacteria in an individual. When using the nucleotide fragments of the invention for such purposes (as described above) in PCR assays, in hybridization assays or in blots, the sequence employed for this purpose should of course be sufficiently specific for the gene which is sought detected. The easiest way to identify sequences having a sufficient specificity is to compare the sequence of the gene with other known sequences (using the databases containing up-dated sequence information) and to choose fragments of the gene which are unique or which would at least react specifically in the chosen assay; as is well-known, the conditions in a hybridization assay may be more or less strict, but it is preferred that the nucleotide sequence used for a hybridization assay is one which will only hybridize under strict conditions, as defined in the art.

As mentioned, in certain aspects, the DNA sequence information provided by the invention allows for the preparation of relatively short DNA (or RNA or PNA) sequences having the ability to specifically hybridize to mycobacterial gene sequences. In these aspects, nucleic acid probes of an appropriate length are prepared based on a consideration of the sequence, e.g., SEQ ID NO: 1. The ability of such nucleic acid probes to specifically hybridize to the mycobacterial gene sequences lend them particular utility in a variety of embodiments. Most importantly, the probes can be used in a variety of diagnostic assays for detecting the presence of pathogenic organisms in a given sample. However, either uses are envisioned, including the use of the sequence information for the preparation of mutant species primers, or primers for use in preparing other genetic constructs.

To provide certainty of the advantages in accordance with the invention, the preferred nucleic acid sequence employed for hybridization studies or assays includes sequences that are complementary to at least a 10 to 40, or so, nucleotide stretch of the selected sequence. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. Thus, one will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production.

As can be seen from example 6, the polypeptides of the invention are also capable of eliciting a Dth response in the form of a skin reaction in guinea pigs. The polypeptides of the invention may thus be useful as agents in a diagnostic skin test.

Therefore, the invention also relates to a method of diagnosing tuberculosis caused by *Mycobacterium tuberculosis, Mycobacterium africanum* or *Mycobacterium bovis* in an animal, including a human being, comprising intradermally injecting, in the animal, a pharmaceutical composition containing a polypeptide as defined above or an analogue and/or subsequence thereof which is immunologically equivalent to the peptide, a positive skin response at the location of injection being indicative of the animal having tuberculosis, and a negative skin response at the location of injection being indicative of the animal not having tuberculosis.

As can be seen from Example 7, the presence of ESAT-6 (one polypeptide of the invention) in short-term culture filtrates from mycobacteria as well as of the esat-6 gene in the mycobacterial genome has been demonstrated to be correlated with the virulence of the mycobacteria from the tuberculosis complex.

Therefore, the diagnostic embodiments of the invention are especially well-suited for performing the diagnosis of ongoing or previous infection with virulent mycobacterial strains of the tuberculosis complex, and it is contemplated that it will be possible to distinguish between 1) subjects (animal or human) which have been previously vaccinated with e.g. BCG vaccines or subjected to antigens from non-virulent mycobacteria and 2) subjects which have or have had active infection with virulent mycobacteria.

A number of possible diagnostic assays and methods can be envisaged:

When diagnosis of previous or ongoing infection with virulent mycobacteria is the aim, a blood sample comprising mononuclear cells (i.a. T-lymphocytes) from a patient could be contacted with a sample of one or more polypeptides of the invention. This contacting can be performed in vitro and a positive reaction could e.g. be proliferation of the T-cells or release cytokines such as γ-interferon into the extracellular phase (e.g. into a culture supernatant). Finally, it is also conceivable to contact a serum sample from a subject to contact with a polypeptide of the invention, the demonstration of a binding between antibodies in the serum sample and the polypeptide being indicative of previous or ongoing infection.

In line with the above, the invention also relates to a method of diagnosing tuberculosis caused by *Mycobacterium tuberculosis, Mycobacterium africanum* or *Mycobacterium bovis* in an animal, including a human being, comprising contacting a blood sample from the animal with a polypeptide of the invention, a significant release into the extracellular phase of at least one cytokine by mononuclear cells in the blood sample being indicative of the animal having or having had tuberculosis. By the term "significant release" is herein meant that the release of the cytokine is significantly higher than the cytokine release from a blood sample derived from a non-tuberculous subject (e.g. a subject which does not react in a traditional skin test for tuberculosis). Normally, a significant release is at least two times the release observed from such a sample.

Alternatively, a sample of a possibly infected organ may be contacted with an antibody raised against a polypeptide of the invention. The demonstration of the reaction between the sample and the antibody will be indicative of ongoing infection.

A further aspect of the invention is a method for immunising a mammal, including a human being, against tuberculosis caused by mycobacteria belonging to the tuberculosis-complex, wherein a vaccine as defined above is administered to the mammal, the vaccine may be administered intravenously, intraperitoneally, intracutaneously or intramuscularly, in doses well-known to the person skilled in the art (cf. the discussion of administration of the vaccines of the invention above).

Another aspect is a monoclonal antibody, which is substantially specifically reacting with a polypeptide as defined above in an immune assay, such as a Western blot or an ELISA test.

In a preferred embodiment the monoclonal antibody is expressed by the deposited cell-line which has been deposited by the applicant Jun. 30, 1993 with the collection of Deutsche Sammlung von Mikroorganismen und Zellkulturen GmbH (DSM) under the accession number DSM ACC2134, or a specifically binding fragment of said antibody.

Yet a another aspect is a nucleotide sequence encoding the antibody described above, such as the nucleotide sequence which is contained in the deposited cell-line described above.

Another aspect is a replicable vector which expresses a polypeptide as defined above. The vector may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication; examples of such a vector are a plasmid, phage, cosmid, mini-chromosome or virus. Alternatively, the vector may be one which, when introduced in a host cell, is integrated in the host cell genome and replicated together with the chromosome(s) into which it has been integrated.

Expression vectors may be constructed to include any of the DNA segments disclosed herein. Such DNA might encode an antigenic protein specific for virulent strains of mycobacteria or even hybridization probes for detecting mycobacteria nucleic acids in samples. Longer or shorter DNA segments could be used, depending on the antigenic protein desired. Epitopic regions of the proteins expressed or encoded by the disclosed DNA could be included as relatively short segments of DNA. A wide variety of expression vectors is possible including, for example, DNA segments encoding reporter gene products useful for identification of heterologous gene products and/or resistance genes such as antibiotic resistance genes which may be useful in identifying transformed cells.

Recombinant vectors such as those described are particularly preferred for transforming bacterial host cells. Accordingly, a method is disclosed for preparing transformed bacterial host cells that includes generally the steps of selecting a suitable bacterial host cell, preparing a vector containing a desired DNA segment and transforming the selected bacterial host cell. Several types of bacterial host cells may be employed, including *E. coli*, *B. subtilis*, as well as rapid-growing mycobacteria such as *M. smegmatis* or even BCG. Also other prokaryotic and eukaryotic host cells may be employed.

Transformed cells may be selected using various techniques, including screening by differential hybridization, identification of fused reporter gene products, resistance markers, anti-antigen antibodies and the like. After identification of an appropriate clone, it may be selected and cultivated under conditions appropriate to the circumstances, as for example, conditions favouring expression or, when DNA is desired, replication conditions.

The present invention therefore further relates to a cell harbouring at least one replicable expression vector as defined above. In principle, this cell may be of any type of cell, i.e. a prokaryotic cell such as a bacterium, e.g. *E. coli* or a *Mycobacterium tuberculosis*, or *Mycobacterium bovis*, or *Mycobacterium africanum*, a unicellular eukaryotic organism, a fungus or yeast, or a cell derived from a multicellular organism, e.g. an animal or a plant. It is especially in cases where glycosylation is desired that a mammalian cell is used, although glycosylation of proteins is a rare event in prokaryotes.

The cell may preferably by a cell which is selected from the group consisting of the lysogenic *E. coli* strains AA226, AA227 and AA242 which have been deposited Jun. 28, 1993 with the collection of Deutsche Sammlung von Mikroorganismen und Zellkulturen GmbH (DSM) under the accession numbers DSM 8377, DSM 8378 and DSM 8379, respectively, in accordance with the provisions of the Budapest Treaty, or a *M. tuberculosis* bovis BCG cell.

A further aspect of the invention is a method for producing a polypeptide as defined above comprising inserting a DNA fragment as defined above into a vector which is able to replicate in a host cell, introducing the resulting recombinant vector into the host cell, culturing the host cell in an appropriate culture medium under appropriate conditions for expressing the polypeptide, and recovering the polypeptide from the host cell or culture medium and optionally subjecting the recovered polypeptide to post-translational modifications, or by isolating the polypeptide from short-term culture filtrate as defined herein.

The medium used to grow the cells may be any conventional medium suitable for the purpose. A suitable vector may be any of the vectors described above, and an appropriate host cell may be any of the cell types listed-above. The methods employed to construct the vector and effect introduction thereof into the host cell may be any methods known for such purposes within the field of recombinant DNA. In the following a more detailed description of the possibilities will be given:

In general, of course, prokaryotes are preferred for the initial cloning of nucleic sequences of the invention and constructing the vectors useful in the invention. For example, in addition to the particular strains mentioned in the more specific disclosure below, one may mention by way of example, strains such as *E. coli* K12 strain 294 (ATCC No. 31446), *E. coli* B, and *E. coli* X 1776 (ATCC No. 31537). These examples are, of course, intended to be illustrative rather than limiting.

Prokaryotes are also preferred for expression. The aforementioned strains, as well as *E. coli* W3110 (F-, lamb-da-, prototrophic, ATCC No. 273325), bacilli such as *Bacillus subtilis*, or other enterobacteriaceae such as *Salmonella typhinurium* or *Serratia marcesans*, and various Pseudomonas species may be used. Especially interesting are rapid-growing mycobacteria, e.g. *M. smegmatis*, as these bacteria have a high degree of resemblance with mycobacteria of the tuberculosis complex and therefore stand a good chance of reducing the need of performing post-translational modifications of the expression product.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (see, e.g., Bolivar et al., 1977, Gene 2: 95). The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the microorganism for expression.

Those promoters most commonly used in recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1979; EPO Appl. Publ. No. 0036776). While these are the most commonly used, other microbial promoters have been discovered and utilized, and details concerning their nucleotide sequences have been published, enabling a skilled worker to ligate them functionally with plasmid vectors (Siebwenlist et al., 1980). Certain genes from prokaryotes may be expressed efficiently in *E. coli* from their own promoter sequences, precluding the need for addition of another promoter by artificial means.

In addition to prokaryotes, eukaryotic microbes, such as yeast cultures may also be used. Saccharomyces cerevisiae, or common baker's yeast is the most commonly used among eukaryotic microorganisms, although a number of other strains are commonly available. For expression in Saccharomyces, the plasmid YRp7, for example, is commonly used (Stinchcomb et al., 1979; Tschemper et al., 1980). This plasmid already contains the trpl gene which provides a selection marker for a mutant strain of yeast lacking the ability to grow in tryptophan for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate in culture (tissue culture) has become a routine procedure in recent years (Tissue Culture, 1973). Examples of such useful host cell lines are VERO and HeLa cells, Chinese hamster ovary (CHO) cell lines, and W138, BHK, COS-7 293 and MDCK cell lines.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication cation (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) or may be provided by the host cell chromosomal replication mechanism. If the vector is integrated into the host cell chromosome, the latter is often sufficient.

In the light of the above discussion the methods for recombinantly producing the polypeptide of the invention are also a part of the invention, as are the vectors carrying and/or being capable of replicating the nucleic acids according to the invention in a host cell or a cell-line. According to the invention the expression vector can be e.g. a plasmid, a cosmid, a minichromosome, or a phage. Especially interesting are vectors which are integrated in the host cell/cell line genome after introduction in the host.

After the recombinant preparation of the polypeptide according to the invention, the isolation of the polypeptide may for instance be carried out by affinity chromatography (or other conventional biochemical procedures based on chromatography), using a monoclonal antibody which substantially specifically binds the polypeptide according to the invention. Another possibility is to employ the simultaneous electroelution technique described by Andersen et al. in J. Immunol. Methods 161: 29–39.

According to the invention the post-translational modifications involves lipidation, glycosylation, cleavage, or elongation of the polypeptide.

The DNA sequence to be modified may be of cDNA or genomic origin as discussed above, but may also be of synthetic origin. Furthermore, the DNA sequence may be of mixed CDNA and genomic, mixed cDNA and synthetic or genomic and synthetic origin as discussed above. The DNA sequence may have been modified, e.g. by site-directed mutagenesis, to result in the desired DNA fragment encoding the desired polypeptide. The following discussion focused on modifications of DNA encoding the polypeptide should be understood to encompass also such possibilities, as well as the possibility of building up the DNA by ligation of two or more DNA fragments to obtain the desired DNA fragment, and combinations of the above-mentioned principles.

The DNA sequence may be modified using any suitable technique which results in the production of a DNA fragment encoding a polypeptide of the invention.

The modification of the DNA sequence encoding the amino acid sequence of the polypeptide of the invention should be one which does not impair the immunological function of the resulting polypeptide.

A preferred method of preparing variants of the antigens disclosed herein is site-directed mutagenesis. This technique is useful in the preparation of individual peptides, or biologically functional equivalent proteins or peptides, derived from the antigen sequences, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art.

In general, site-directed mutagenesis in accordance herewith is performed by first obtaining a single-stranded vector which includes within its sequence a DNA sequence which encodes the polypeptides of the invention. An oligonucleotide primer bearing the desired mutated sequence is prepared, generally synthetically, for example by the method of Crea et al. (1978). This primer is then annealed with the single-stranded vector, and subjected to DNA polymerizing enzymes such as $E.\ coli$ polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as $E.\ coli$ cells, and clones are selected which include recombinant vectors bearing the mutated sequence arrangement.

The preparation of sequence variants of the selected nucleic acid fragments of the invention using site-directed mutagenesis is provided as a means of producing potentially useful species of the genes and is not meant to be limiting as there are other ways in which sequence variants of the nucleotide fragments of the invention may be obtained. For example, recombinant vectors encoding the desired genes may be treated with mutagenic agents to obtain sequence variants (see, e.g., a method described by Eichenlaub, 1979) for the mutagenesis of plasmid DNA using hydroxylamine.

Analogues/subsequences of the disclosed nucleic acid fragments which also form part of the invention are nucleic acid fragments which are fused to at least one other nucleic acid fragment which encodes a protein enhancing the immunogenicity of the fused protein relative to a protein without the encoded fusion partner. Such encoded proteins may e.g. be T-cell epitopes or other immunogenic epitopes enhancing the immunogenicity of the target gene product, e.g. lymphokines such as INF-γ, IL-2 and IL-12.

Other nucleic acid fragments to form part of a nucleic acid fragment of the invention encoding a fusion polypeptide are those encoding polypeptides which facilitate expression and/or purification of the fused peptide, e.g. bacterial fimbrial proteins, e.g. the pilus components pilin and papA; protein A; the ZZ-peptide; the maltose binding protein; gluthatione S-transferase; β-galactosidase; or polyhistidine.

The polypeptide of the invention may alternatively be produced by the well-known methods of solid or liquid phase peptide synthesis utilizing the successive coupling of the individual amino acids of the polypeptide sequence or coupling of individual amino acids forming fragments of the polypeptide sequence so as to result in the desired polypeptide.

A yet further aspect of the invention is a method for producing a vaccine according as defined above, comprising producing or isolating a polypeptide as defined above, and solubilizing or dispersing the polypeptide in a medium for a vaccine, and optionally adding other $M.\ tuberculosis$ antigens and/or an adjuvant substance, or cultivating a cell from a microorganism comprising at least one nucleotide sequence as described above, and transferring the cell to a medium for a vaccine, and optionally adding an adjuvant substance.

LEGENDS TO FIGURES

FIG. 1: Course of infection with *M. tuberculosis* in naive and memory immune mice. C57Bl/6j mice were infected with $2.5\times10^5$ viable units of *M. tuberculosis* and the growth of the organisms in the spleen was investigated for a period of 25 days. The count of the CFU indicated represent the means of 4–5 mice.

FIG. 2: In vivo IFN-γ production during tuberculosis infection. Memory immune or naive mice were infected with $2.5\times10^5$ colony forming units of *M. tuberculosis* i.v. and the level of IFN-γ was monitored in the spleen or serum of animals during the course of infection.

FIG. 3: In vitro response of spleen lymphocytes from infected mice. Memory immune or naive mice were sacrificed at different time points during the course of infection, and spleen lymphocytes were stimulated in vitro with ST-CF or killed bacilli. Cell culture supernatants were tested for the presence of IFN-γ.

FIG. 4: Short-term culture-filtrate fractions. ST-CF was divided into 14 fractions by the multi-elution technique and the fractions were analyzed by SDS-PAGE and Silver-staining. Lane F: ST-CF Lane 1–15: fractions 1–15.

FIG. 5: T-cell reactivation during a secondary infection. IFN-γ release by spleen lymphocytes isolated either directly from memory immune mice or four days after the mice had received a secondary infection. The lymphocytes were stimulated in vitro with ST-CF fractions and the supernatants harvested for quantification of IFN-γ. The migration of molecular mass markers (as shown in FIG. 4) are indicated at the bottom.

FIG. 6: Precise mapping of IFN-γ release in response to single secreted antigens. A panel of narrow fractions within the stimulatory regions 4–14 and 26–34 enabled the precise mapping of proteins capable of inducing IFN-γ in microcultures containing lymphocytes from memory immune mice at day 4 of rechallenge. On the left hand side: IFN-γ release by single secreted antigens. On the right hand side: The localization of and IFN-γ induction by defined secreted antigens of *M. tuberculosis*. ST-3, 76–8 and PV-2 are the designation of three mAbs which defines secreted antigens of molecular mass 5–8 kDa.

Figure 7:
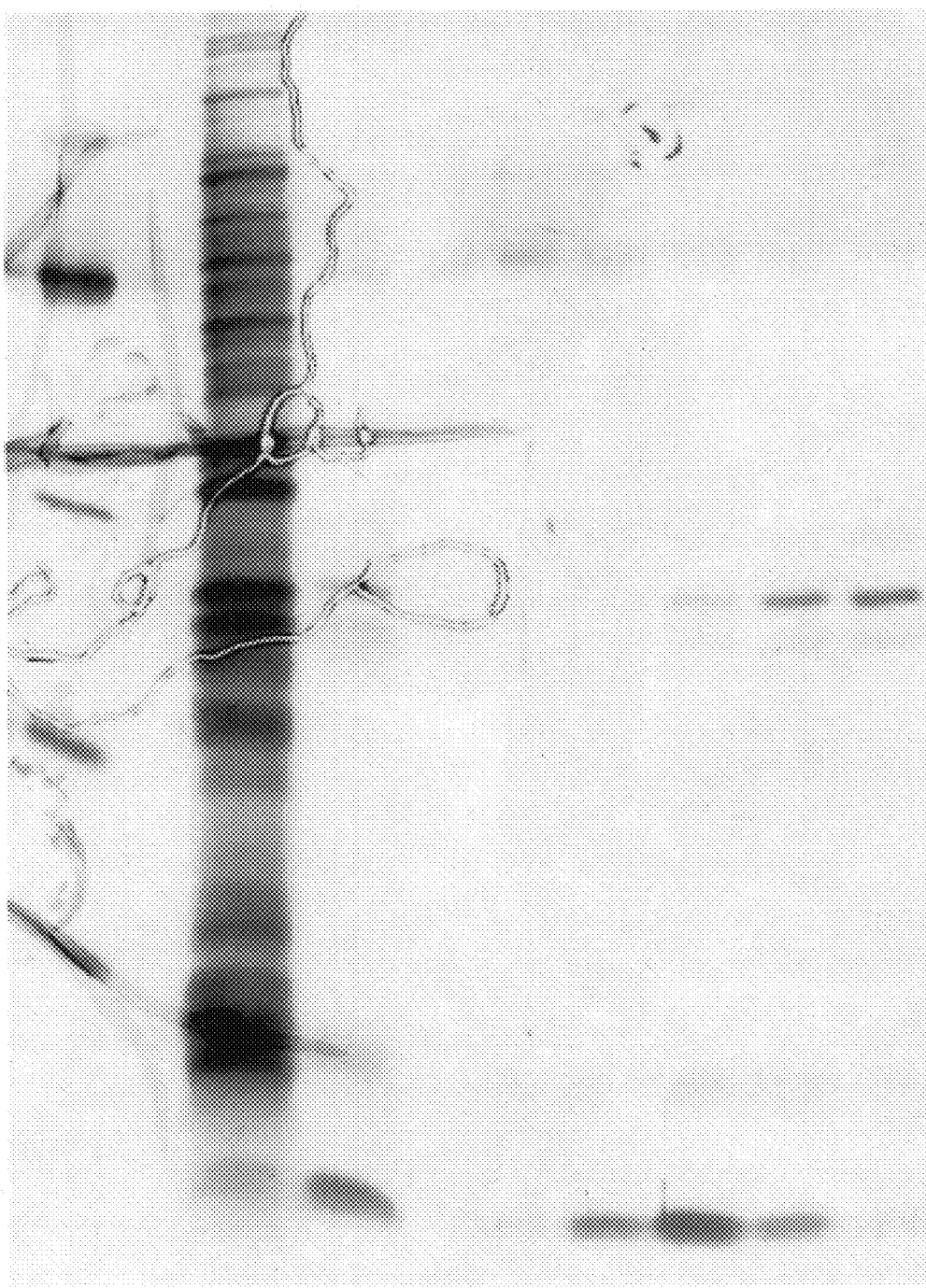

FIG. 7: Biochemical purification of HYB76-8 reactive antigen (ESAT6). SDS-PAGE analysis of purified ESAT6 obtained from a three step purification method involving a final gel filtration on a Superdex 75 column. The sample applied to the column was the HYB76-8 reactive antigen containing fraction eluted from the Mono Q column during the 2nd purification step. Lanes 5, 6, and 7 show the presence of the HYB76-8 reactive antigen in the region below the 14.4 kDa molecular weight marker.

Figure 8:
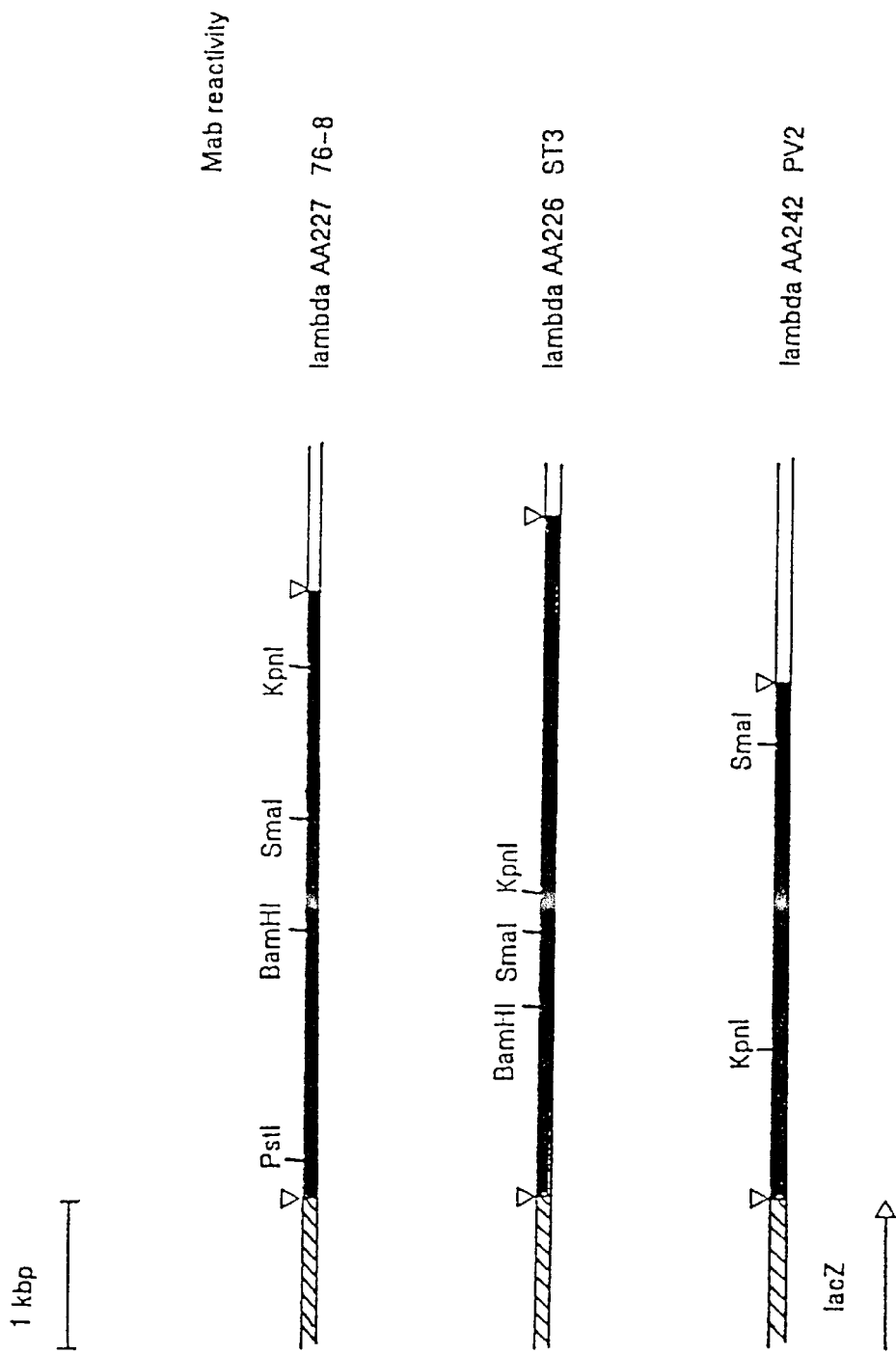

FIG. 8: Physical map of recombinant lambda phages expressing products reactive with Mabs recognizing low MW components. Cross-hatched bar; lacZ, solid bar; *M. tuberculosis* DNA, open bar; lambdagt11 DNA (right arm), open triangles indicate EcoRI cleavage sites originating from the lambdagt11 vector. The direction of translation and transcription of the gene products fused to beta-galactosidase is indicated by an arrow.

FIGS. 9A and 9B: Western blot analyses demonstrating recombinant expression of low molecular weight components. Lysates of *E. coli* Y1089 lysogenized with lambda AA226, lambda AA227 or lambda were analyzed in Western blot experiments after PAGE (A: 10%, B: 10 to 20% gradient). FIG. 9A: lanes 1: lambda gt11, lanes 2: lambda AA226, lanes 3: lambda AA227.

FIG. 9B: lane 1: lambda gt11, lanes 2 and 3: lambda AA242 and AA230 (identical clones). The monoclonal antibodies are indicated on top of each panel. L24, c24 is an anti-MPT64 reactive monoclonal antibody.

Figure 10A:
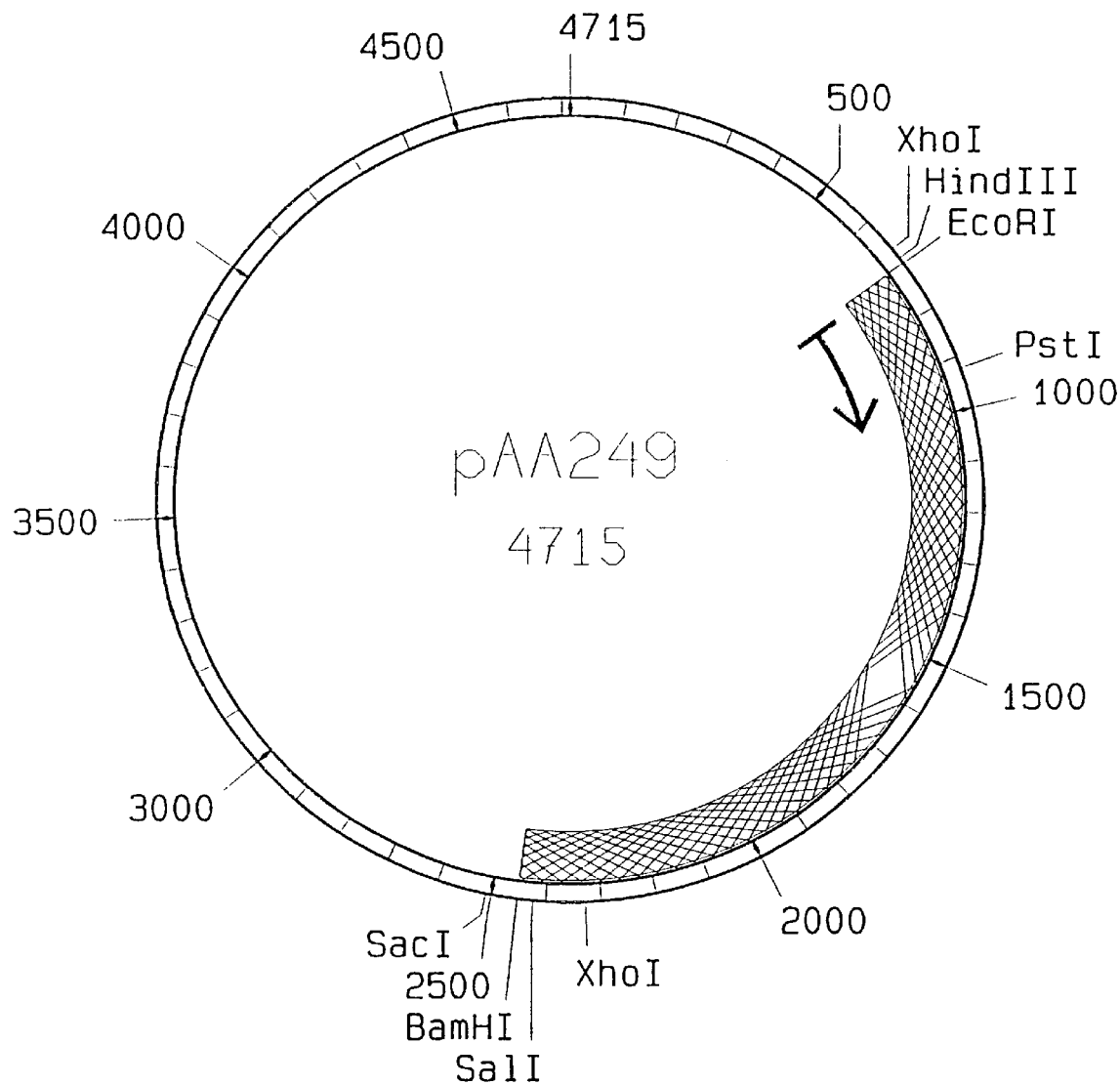

FIGS. 10A, 10B, and 10C: Recombinant ESAT6. 10A: Plasmid map of pAA249. The 1.7 kbp EcoRI—BamHI fragment of lambda AA227 subcloned into EcoRI—BamHI sites of pBluescript. Cross-hatched bar; mycobacterial DNA, Arrow; the esat6 gene. 10B: The complete DNA sequence of the mycobacterial DNA of pAA249. The sequence is obtained by the dideoxy sequencing method (Sanger, F. et al. 1977, DNA sequencing with chain terminating inhibitors. Proc. Natl. Acad. Sci. 74: 5463) and cycle sequencing using the Dye Terminator system in combination with the automated gel reader, model 373A from Applied Biosystems; the sequence is also shown in SEQ ID NO: 1. ESAT6 is encoded by the DNA sequence from the ATG start codon at position 13–15 to the TAG stop codon at position 298–300. 10C: The deduced amino acid sequence of ESAT6 (also shown in SEQ ID NO: 2) in conventional three letter code. The * indicate amino acids which could be aligned to the sequence obtained by N-terminal sequencing of biochemically purified native material.

Figure 11:
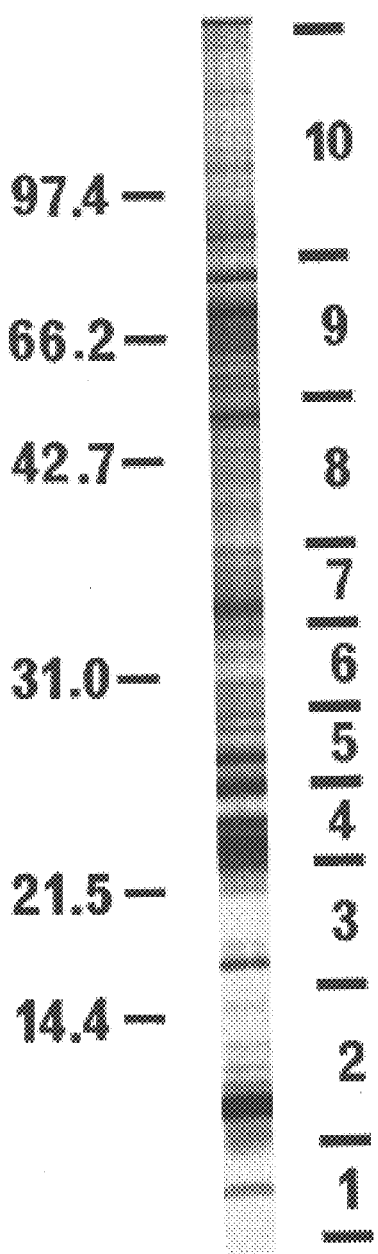

FIG. 11: ST-CF fractions for investigation of T cell response patterns in genetically heterogeneous animals. ST-CF were separated in SDS-PAGE and silver stained. MW markers are indicated to the left and the cut-offs used in the preparation of fractions 1–10 to the right. These fractions were used for the experiments indicated in FIGS. 12 and 13.

Figure 12A:
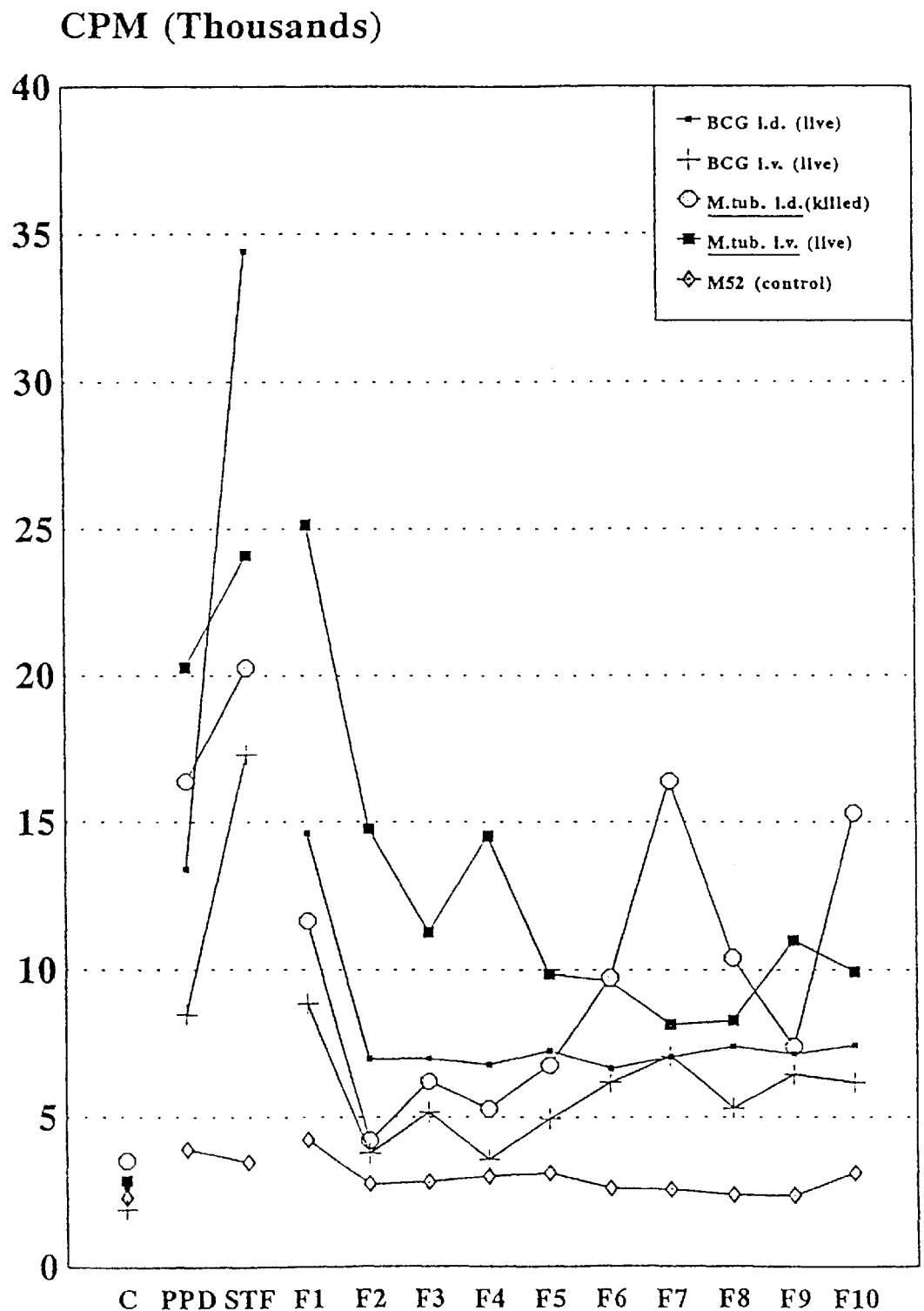
Figure 12B:
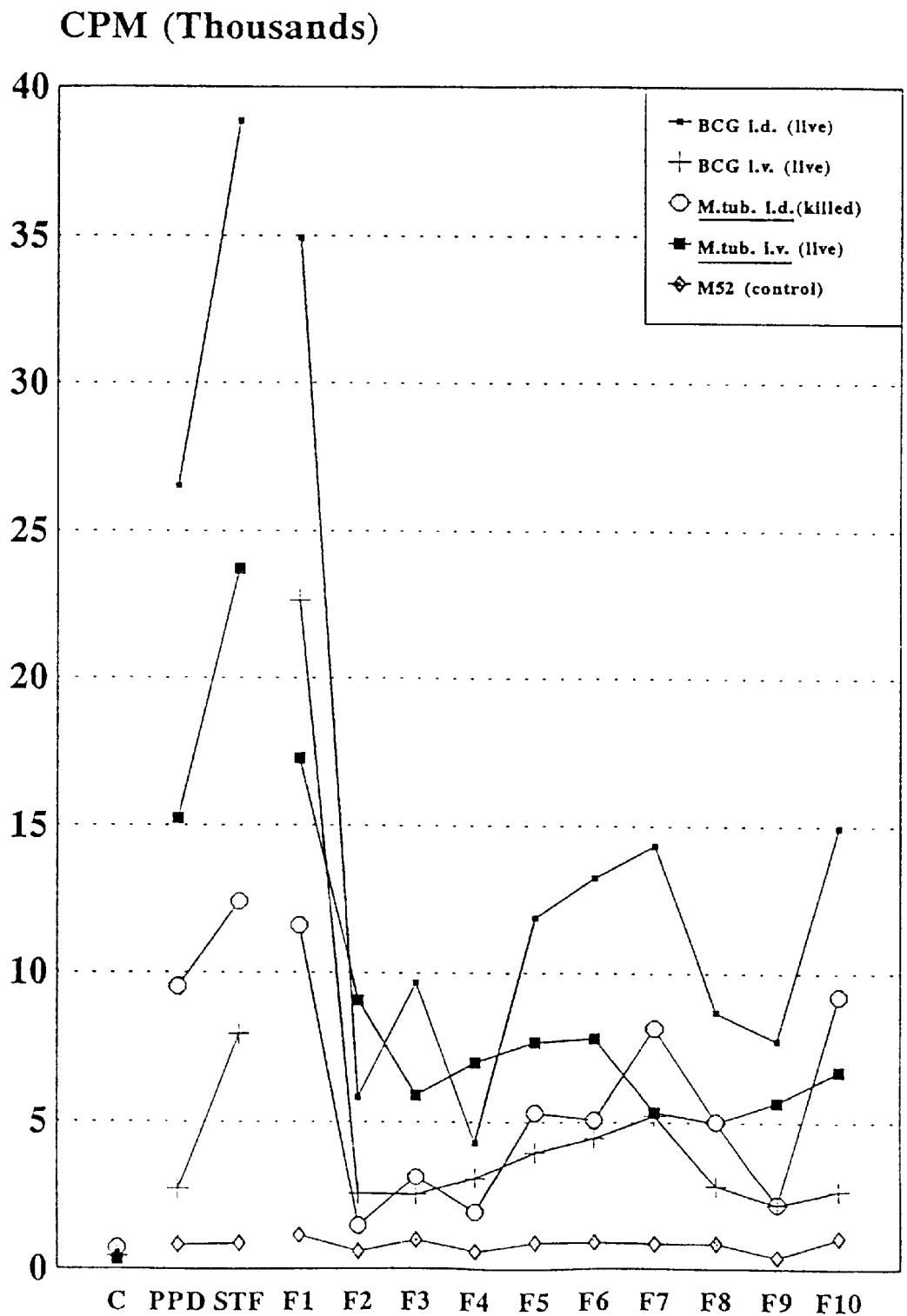

FIGS. 12A and 12B: Guinea pig responses to ST-CF fractions. Lymphocyte stimulation results with spleen lymphocytes (FIG. 12A) and peripheral blood lymphocytes (FIG. 12B). The cells were not stimulated (C) or stimulated with 1 μg of fractions 1–10 (F1–F10) or with PPD and ST-CF. The stimulations are means from groups of 8–10 guinea pigs sensitized as indicated in the figure insert.

Figure 13:
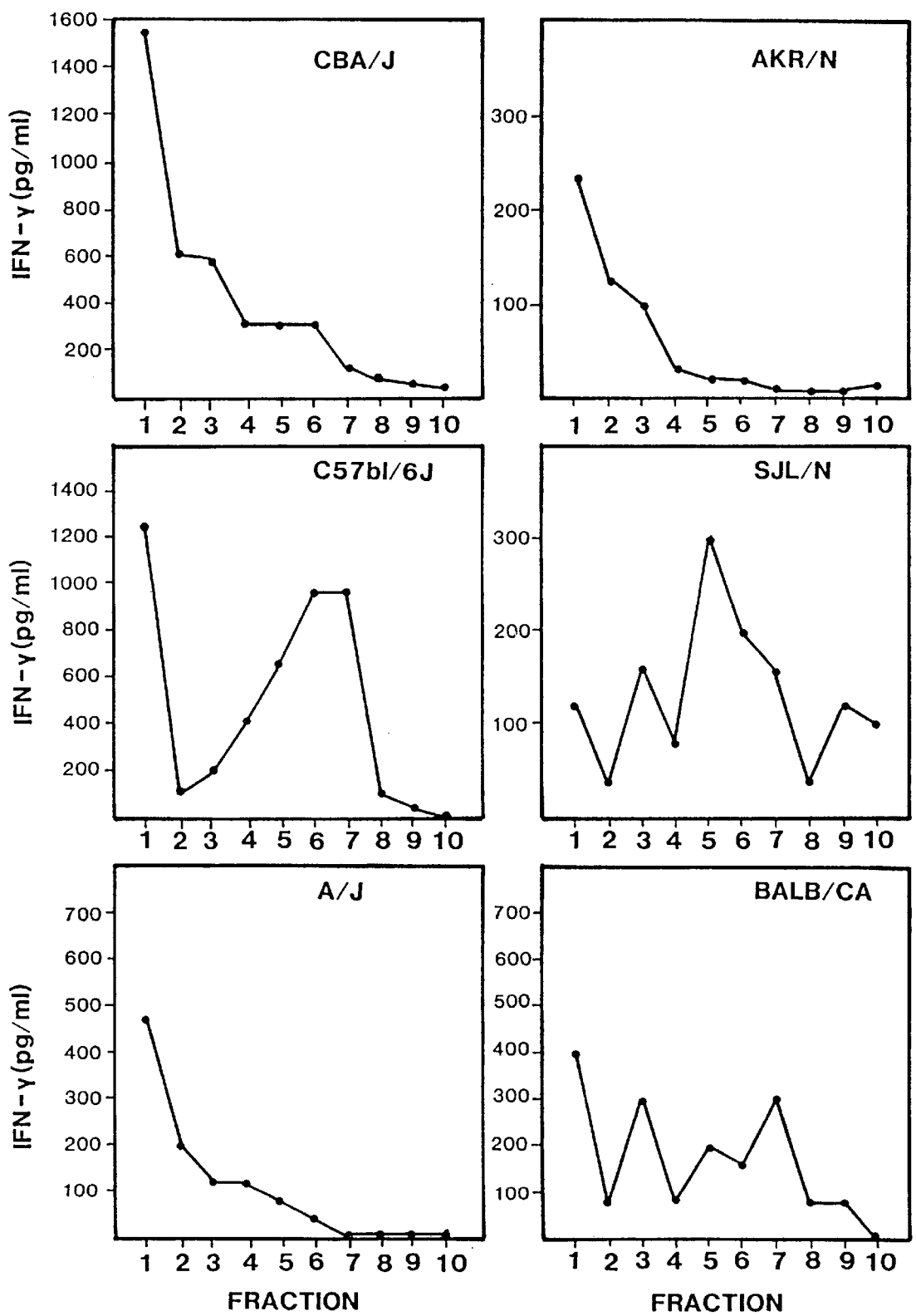

FIG. 13: T cell responses in different strains of inbreed mice. Mouse T cells were stimulated in vitro with the panel of STCF fractions and IFN-γ release to the culture supernatants monitored.

Figure 14:
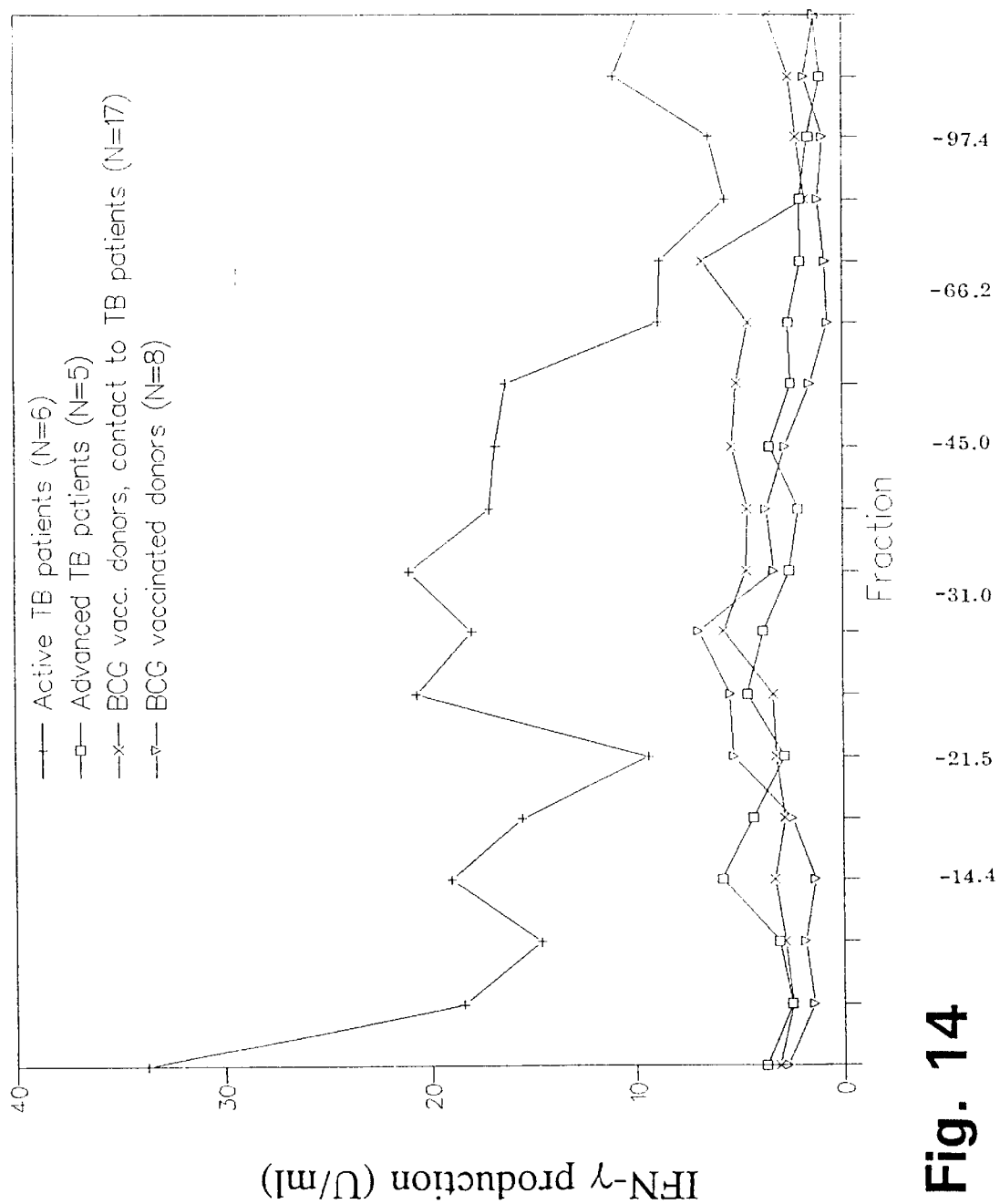

FIG. 14: Human IFN-γ response to ST-CF fractions. Human PBL were stimulated in vitro with ST-CF fractions and cell culture supernatants investigated for the presence of IFN-γ.

Figure 15:
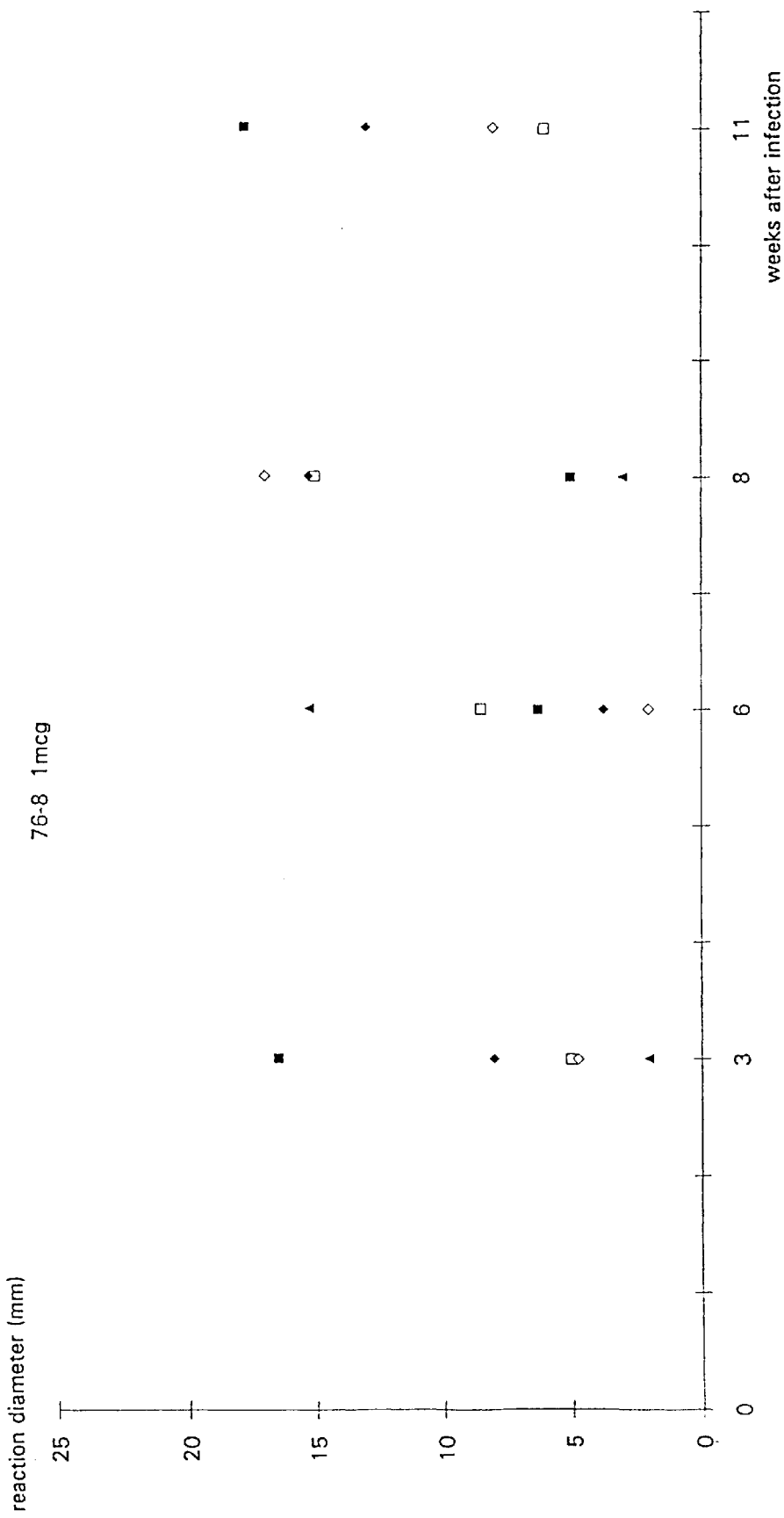

FIG. 15: The skin test inducing capacity of purified, native ESAT6 in aerosol infected guinea pigs.

The diameter of skin test reactions was measured 3, 6, 8, and 11 days after exposure of 4 groups of guinea pigs (N=5) to aerosols of *M. tuberculosis*.

PREAMBLE TO EXAMPLES

It is an established fact that long-term immunological memory resides after termination of a tuberculous infection (Orme, I. M. 1988., Lefford, M. J. et al. 1974.). This memory immunity efficiently protects the host against a secondary infection with M. tuberculosis later in life. When an immune host mounts a protective immune response, the specific T-cells responsible for the early recognition of the infected macrophage, stimulates a powerful bactericidal activity through their production of IFN-γ (Rook, G.A.W. 1990., Flesch, I. et al. 1987.). Protective antigens which are to be incorporated in a future sub-unit vaccine have in the examples below been sought among the molecular targets of the effector cells responsible for the recall of a protective immune response. This has resulted in the identification of immunodominant antigenic targets for T-cells during the first phase of a protective immune response.

Bacteria. *M. tuberculosis* H37Rv (ATCC 27294) was grown at 37° C. on Löwenstein-Jensen medium or in suspension in modified Sauton medium. BCG Copenhagen was obtained as a freeze dried vaccine and were rehydrated with diluted sauton followed by a brief sonication to ensure a disperse suspension.

Production of short-term culture filtrate (ST-CF). ST-CF was produced as described previously (Andersen et al., 1991b). Briefly *M. tuberculosis* ($4\times10^6$ CFU/ml) were incubated in Sauton medium and grown on an orbital shaker for 7 days. The bacteria were removed by filtration and the culture supernatants were passed through sterile filters (0.2 μm) and concentrated on an Amicon YM 3 membrane (Amicon, Danvers, Mass.).

Fractionation of ST-CF by the multi-elution technique. ST-CF (5 mg) was separated in 10–20% SDS-PAGE overnight (11 cm vide centerwell, 0.75 mm gel). After the termination of the electrophoretic run the gel was trimmed for excess gel, and pre-equilibrated in 3 changes of 2 mM phosphate buffer for 40 min. The multi-elution was performed as described previously (Andersen and Heron, 1993b). Briefly, gels were transferred to the Multi-Eluter™ (KEM-EN-TECH) and electroeluted (40 V) into 2 mM phosphate buffer for 20 min. The polypeptide fractions were aspirated and adjusted to isotonia with concentrated PBS. All fractions were stabilized with 0.5% mice serum and were kept frozen at -80° C. until use.

Lymphocyte cultures. Lymphocytes were obtained by preparing single-cell suspensions from spleens as described in Andersen et al., 1991a. Briefly, ST-CF or antigenic fractions were added to microcultures containing $2\times10^5$ lymphocyte in a volume of 200 μl Rpmi 1640 supplemented with $5\times10^5$ M 2-mercaptoethanol, penicillin, streptomycin, 1 mM glutamine and 0.5% (vol/vol) fresh mouse serum.

ST-CF was used in the concentration 4 μg/ml while ST-CF fractions were used in 1 μg/ml.

Cellular proliferation was investigated by pulsing the cultures (1 μCi [$^3$H] thymidine/well) after 48 h of incubation, further incubating the plates for 22 hours and finally harvesting and processing the plates for liquid scintillation counting (Lkb, Beta counter). Culture supernatants were harvested from parallel cultures after 48 hours incubation and used for lymphokine analyses.

Lymphokine analyses. The amount of INF-γ present in culture supernatants and in homogenised organs was quantified by an IFN-γ ELISA kit (Holland Biotechnology, Leiden, the Netherlands). Values below 10 pg were considered negative.

Example 1

Isolation of T-cell stimulating low molecular weight ST-CF antigens

A group of efficiently protected mice was generated by infecting 8–12 weeks old female C57Bl/6j mice bred at Statens Seruminstitut, Copenhagen, Denmark, with $2.5\times10^3$ *M. tuberculosis* i.v. After 30 days of infection the mice were subjected to 60 days of antibiotic treatment with isoniazid and were then left for 200–240 days to ensure the establishment of resting long-term memory immunity. The mice were then reinfected with $2.5\times10^5$ *M. tuberculosis* i.v. and the course of infection was compared with that of a corresponding naive group of mice (FIG. 1).

As seen in FIG. 1, *M. tuberculosis* grow rapidly in the spleens of naive mice whereas the infection is controlled within the first few days in memory immune mice. This finding emphasizes that early immunological events occurring during the first days determines the outcome of infection.

Gamma interferon (IFN-γ) is a lymphokine which is involved directly in protective immunity against *M. tuberculosis* (Rook G. A. W., 1990, Flesch I. and Kaufmann S., 1987). To monitor the onset of a protective immune response, the content of IFN-γ in spleen homogenates (4% w/v in PBS) and in serum samples was investigated during the course of infection (FIG. 2). Memory immune mice were found to respond immediately (<24 h) by a marked production of IFN-γ detectable both in spleen and in serum. Naive mice, in contrast, had a 14 days delay before any significant production was evident, a period during which infection rapidly progressed. Immune mice were characterized by an accelerated release of IFN-γ and to determine the molecular targets of this immunological response, spleen lymphocytes were obtained from animals at different time points during the course of infection. The lymphocytes were stimulated in vitro with either bacteria, killed with glutaraldehyde and washed with PBS or short-term culture-filtrate (ST-CF) which is a complex mixture of proteins secreted by *M. tuberculosis* during growth (Andersen, P. et al. 1991.) (FIG. 3). The memory immune mice were found to be characterized by an accelerated generation of IFN-γ producing T-cells responding to ST-CF whereas killed bacteria in contrast were found to elicit only a marginal response at a very late stage of infection.

To map the molecular targets of protective T-cells among the multiple secreted proteins present in ST-CF a screening of ST-CF was performed using the multi-elution technique (Andersen and Heron, 1993b). This technique divides complex protein mixtures separated in SDS-PAGE into narrow fractions in a physiological buffer (FIG. 4). These fractions were used to stimulate spleen lymphocytes in vitro and the release of IFN-γ was monitored (FIG. 5). The response of long-term memory immune mice (the mice were left for 200–240 days to ensure immunological rest) was compared to the response generated after 4 days of rechallenge infection. This comparison enable the mapping of targets for memory effector T-cells triggered to release IFN-γ during the first phase of a protective immune response. Using this approach it was demonstrated that the targets for these protective T-cells were secreted proteins or fragments of proteins of apparent molecular mass 6–10 and 26–34 kDa (FIG. 5).

To precisely map single molecules within the stimulatory regions the induction of IFN-γ by a panel of narrow overlapping fractions was investigated. This enabled the identification of a 6–8 kDa protein fraction with exceedingly stimulatory capacity (5100–5400 pg IFN-γ units/ml) (FIG. 6). The 6-kDa protein band yielding the highest release of IFN-γ (5390 pg/ml) was recognized by the mAb HYB76-8, whereas the adjacent protein bands were recognized by the mAbs ST-3 and PV-2.

The mAb HYB76-8 which therefore defines the major target for protective T-cells was used to identify the antigen during a 3 step column chromatography:

1. Hydrophobic interaction chromatography.

3M ammonium sulphate in phosphate buffer was added to ST-CF (lane 1, FIG. 7) (1–10 mg/ml) so as to obtain a final concentration of 1M ammonium sulphate. The precipitated proteins were removed by centrifugation, and the supernatant applied to a Phenyl Sepharose CL-4B (Pharmacia) column (Pharmacia Fine Chemicals, Uppsala, Sweden). Western blot analysis at this point shows that the HYB76-8 reactive antigen was primarily present in the supernatant. A linear gradient of decreasing concentration of ammonium sulphate (a linear gradient 1M—0M ammonium sulphate, in 50 mM phosphate buffer (pH 8.5) was run. The HYB76-8 reactive antigen was eluted at concentrations of 100 mM—0 mM ammonium sulphate.

2. Anion exchange chromatography.

Fractions containing HYB76-8 reactive antigen were collected and submitted to buffer exchange. The buffer used was a 50 mM TRIS/HCl, pH 8.5. The sample was run on a Mono Q (Pharmacia) using a linear gradient of 0–0.5 NaCl. The HYB76-8 reactive antigen was eluted at a NaCl concentration of 150–200 mM NaCl.

3. Gel filtration.

HYB76-8 reactive antigen fractions were applied directly to a Superdex 75 16/60 column (Pharmacia), 3 ml per run. The buffer used was PBS, pH 7.4. Half of the HYB76-8 reactive antigen containing fractions collected contain GroES as the only other antigen (lanes 5, 6, and 7 in FIG. 7).

Results obtained from experiments similar to those of example 1 have further pointed to the protein recognized by the mAb HYB76-8 as an important antigen in the early response to reinfection with *M. tuberculosis*. In experiments with T-cell suspensions from rechallenged mice it was demonstrated that chemically purified HYB76-8 reactive antigen elicited an exceedingly high release of IFN-γ (13933±836 pg/ml at a protein concentration of 20 μg/ml). ST-CF in comparison did in this experiment induce a release of 7300±208 pg/ml. Recombinant HYB76-8 reactive antigen did in such experiments elicit a somewhat lower release of IFN-γ(3500–5000 pg/ml).

Example 2

Vaccination with a ST-CF containing vaccine

The results in example 1 pinpoints ST-CF as target for T-cells involved in protective immunity, a finding which was further confirmed by investigating the protective efficacy of an experimental vaccine based on ST-CF:

Female, 8–12 weeks old C57Bl/6j mice bred at Statens Serum Institute, Copenhagen, Denmark, were immunized with $5 \times 10^4$ CFU of BCG s.c in 0.2 ml saline at the base of the tail. This dose was found to induce an optimal protective immune response in our animal model (results not shown).

The experimental vaccines which contained 100 mg ST-CF/dose and applied dimethyldioctadecylammonium bromide (DDA) (250 mg/dose) as adjuvant in 0.2 ml were given S.C. three times with weekly intervals at different sites on the back of the mice to boost a strong cellular immune response to ST-CF.

DDA (Eastmann Kodak, USA) was prepared by suspension of the powder in distilled water (2.5 mg ml$^{-1}$). A fine homogenous dispersion of the powder was obtained by heating the suspension to 80° C. for 5–10 minutes. After cooling at room temperature the suspension was mixed with equal amount of either PBS or diluted ST-CF. Each injection contained 250 µg of DDA in 0.2 ml.

In the first series of protection experiments the mice were left for 12–14 weeks after the first injection and were then challenged by an i.v. injection of $1 \times 10^4$ viable *M. tuberculosis*. The course of the disease was monitored in the spleens and lungs at different time points during the first 28 days.

In the second series of protection experiments the mice were challenged 5–6 weeks after the first injection by an i.p. injection of $1 \times 10^6$ *M. tuberculosis*.

After 2–3 weeks of infection the mice were killed and the number of viable bacteria in the spleens of infected mice was determined by plating double serial 10-fold dilutions of organ homogenates on Lowenstein-Jensen medium. Colonies were counted after 3 to 4 weeks of incubation, and the data were expressed as the log$_{10}$ values of the geometric means of counts obtained with six to twelve mice (Table 1).

TABLE 1

Bacterial numbers in organs of vaccinated mice receiving a challenge of virulent *M. tuberculosis*

| Immunization[a] | Experiment 1[b] | | Experiment 2[b] |
|---|---|---|---|
| | Spleen | Lung | Spleen |
| Control | 5.41 | 3.61 | 4.83 |
| BCG | 4.00 (P = 0.0001) | 2.94 (P = 0.0012) | 2.96 (P = 0.0002) |
| ST-CF and PBS | 5.48 | 3.70 | ND |
| PBS and DDA | 5.18 | 4.03 | 4.38 |
| ST-CF and DDA | 4.17 (P = 0.0001) | 2.93 (P = 0.0026) | 3.46 (P = 0.0042) |

[a]Mice were immunized with BCG or injected three times with the experimental vaccines.
[b]Bacterial numbers are expressed as the log 10 values of the geometric means (n = 6 in experiment 1 and n = 12 in experiment 2). SEM is less than 0.16 in experiment 1 and less than 0.32 in experiment 2. P values have been given for bacterial numbers that are significantly different from the numbers found for unimmunized control animals.

These experiments convincingly demonstrated that ST-CF contains protective antigens which can be used to boost a long-term memory immune response of the same protective efficacy as the one provided by live BCG.

Example 3

Construction of a vaccine based on selected secreted antigen fractions.

Figure 5:
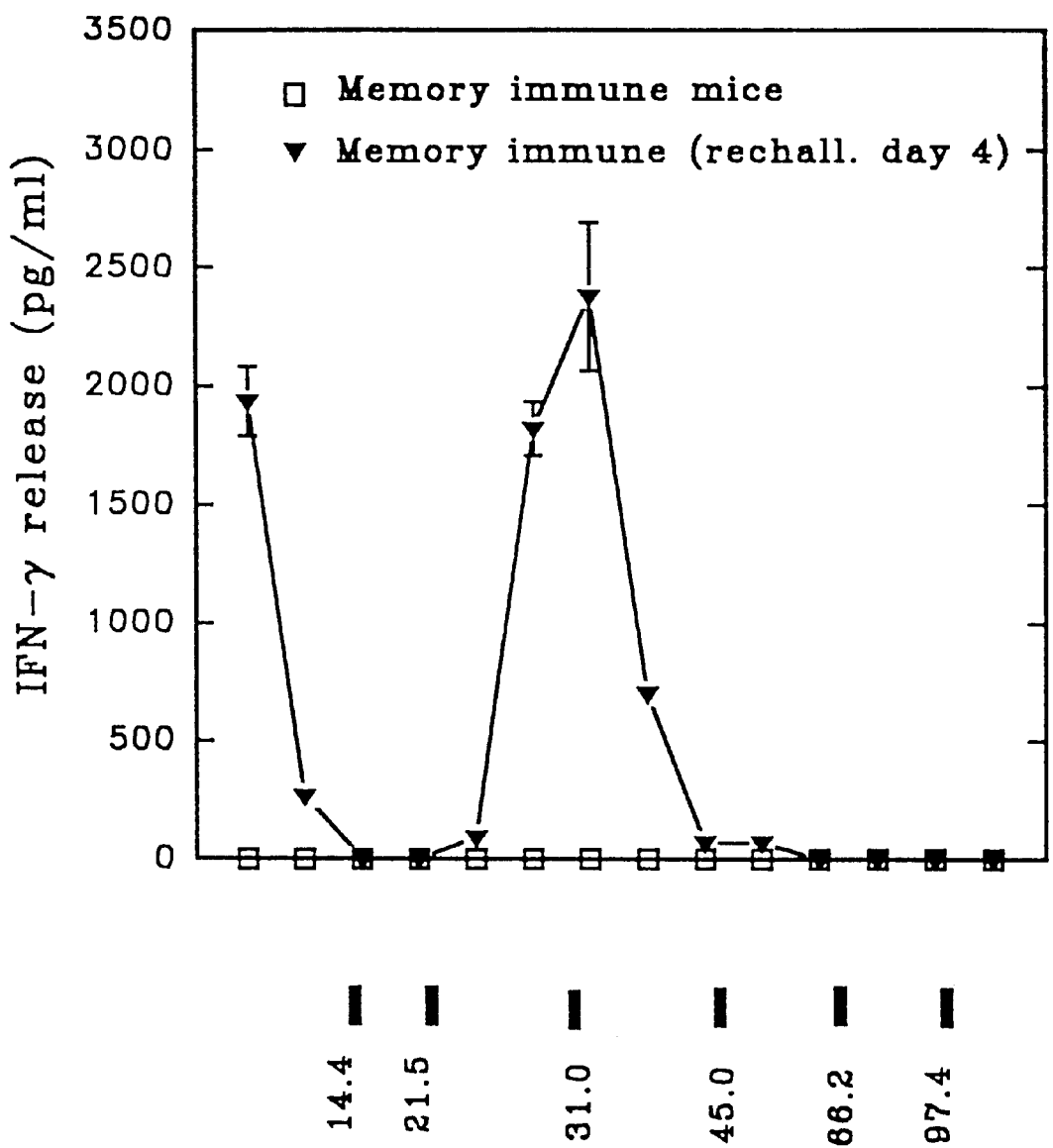
Figure 6:
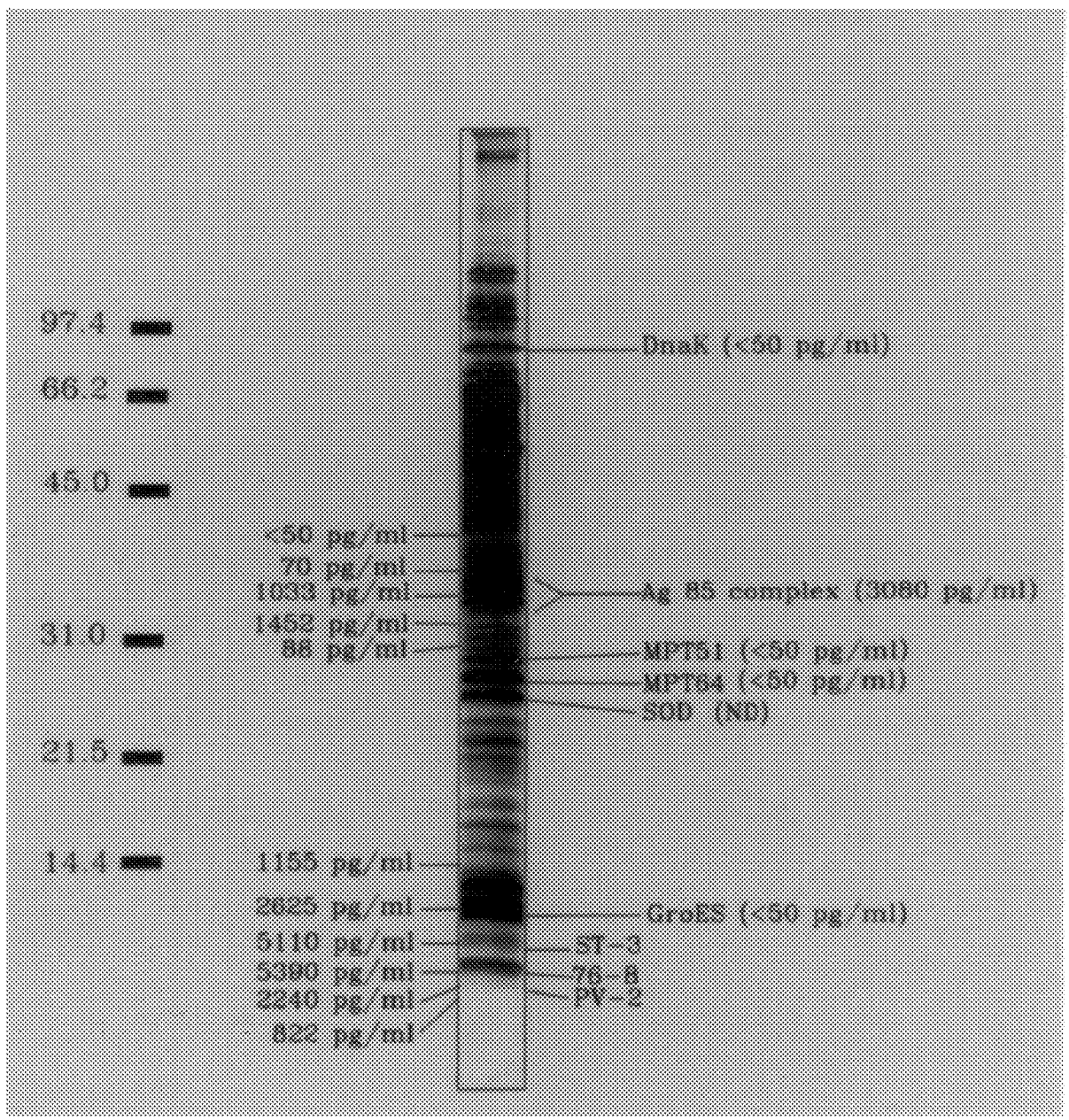

The molecular targets for INF-γ producing T cells involved in the first phase of a protective immune response were found within the region 6–10 and 26–34 kDa of ST-CF (FIG. 5). An experimental vaccine based on these selected antigen fractions and the adjuvant DDA was therefore constructed and tested in our animal model. In addition this experiment included vaccines based on the two single antigenic targets identified so far; the 31–32 kDa antigen 85 and a recombinant version of the 6 kDa antigen.

Vaccinated mice were left for 12–14 weeks after the first injection and were then challenged by an i.v. injection of $1 \times 10^4$ viable *M. tuberculosis*. Mice were killed and bacteria enumerated as in the previous experiment (table 2).

TABLE 2

Bacterial numbers in spleens of mice vaccinated with fractions of ST-CF and challenged with *M. tuberculosis*

| Immunization[a] | Bacterial numbers[b] |
|---|---|
| Control | 5.17 |
| BCG | 3.51 |
| PBS and DDA | 4.75 |
| ST-CF (6–10 kDa) and DDA | 4.33 |
| ST-CF (26–34) and DDA | 4.02 |
| Ag 85 and DDA | 4.85 |
| REC HYB76-8 reactive antigen and DDA | 4.90 |

[a]Mice were immunized with BCG or injected three times with experimental vaccines.
[b]Bacterial numbers are expressed as the log 10 values of the geometric means. SEM are less than 0.30.

The experiment demonstrated that both the vaccine based on the antigenic fractions ranging from 6–10 and the vaccine based on the antigenic fractions from 26–34 kDa induced an increased level of acquired resistance, a result which emphasizes the presence of protective antigens within these regions of ST-CF.

Neither purified Ag 85 or the 6 kDa antigen, however induced any significant protection in this experiment. The reason for the low efficacy of these vaccines based on the purified products was pursued by investigating the T cell subsets induced by the immunization. T cells were isolated from the vaccinated mice and stimulated in vitro with ST-CF. Cellular proliferation in the cultures were investigated and the release of IFN-γ quantified. This experiment demonstrated that although all the different vaccination protocols induced T cells proliferating in response to ST-CF in vitro exceedingly low levels of IFN-γ(<50 pg/ml) were present in the cultures with T cells from mice immunized with the purified proteins (the 6 kDa and Ag 85). Cells derived from mice immunized with a mixture of the complex mixture of ST-CF and DDA in contrast, released 1800–2000 pg/ml of IFN-γ.

This result strongly suggests that whereas a vaccine based on the mixture of proteins contained within ST-CF induces a protective immune response consisting predominantly of Th-1 cells characterized by the release of high levels of IFN-γ and IL-2 and low levels of IL-4 and IL-5 (results not shown), a similar vaccine based on single purified products are characterized by the induction of a response biased towards non-protective Th-2 cells not capable of producing IFN-γ. A possible explanation on this discrepancy may be that molecules with adjuvant properties (immunomodulators) exist among the proteins present in ST-CF. The work has therefore been continued with the purpose of establishing an adjuvant system capable of inducing a powerful IFN-γ response, even with purified products. DDA has been combined with recombinant IFN-γ or the synthetic IFN-γ inducer poly-IC. These mixtures have been mixed with ST-CF, mice immunized and the reactivity of the T cells induced has been investigated by stimulating T cell suspensions in vitro with ST-CF (table 3).

TABLE 3

Recall reactivity in Vitro after immunization with ST-CF in different adjuvant combinations

| Immunization | Proliferation (CPM) | IFN-γ (pg/ml) |
|---|---|---|
| DDA | 8820 | 325 |
| DDA/IFN-γ (10000 U) | 30988 | 2933 |
| DDA/poly I:C (100 μg) | 40851 | 3000 |

This experiment demonstrated that both of these additions induced an enhanced T cell proliferative response associated with markedly increased levels of IFN-γ.

This line of research will be continued (eg. by the addition of other recombinant cytokines) or testing of alternative adjuvant systems. The criteria used for determining the feasibility of an adjuvant will be the induction of an efficient Th-1 response as judged by:

1) High IFN-γ/IL-4 ratio during in vitro recall response.
2) High IFN-γ/IL-4 mRNA ratio induced in the regional lymphnodes.
3) High IgG2a/IgG1 ratio in specific immunoglobulin induced by the immunization.
4) High efficacy of the vaccine against a subsequent challenge.

The purified proteins will subsequently be tested in the optimal adjuvant combination.

Example 4

Cloning of genes expressing HYB76-8, PV-2 and ST-3 binding proteins.

It was demonstrated (in example 1) that low molecular weight components (components with an apparent molecular weight less than that of GroES) in short-term culture filtrate reacted with the monoclonal antibodies produced by the three hybridomas ST-3, HYB76-8, and PV-2. In order to identify the antigens binding to these antibodies, the following experiments were carried out:

The recombinant λgt11 *M. tuberculosis* DNA library constructed by R. Young (Young, R. A. et al. 1985) and obtained through the World Health Organization IMMTUB programme (WHO.0032.wibr) was screened for phages expressing gene products which would bind the monoclonal antibodies HYB76-8, PV-2 and ST-3.

Approximately $1 \times 10^5$ pfu of the gene library (containing approximately 25% recombinant phages) were plated on *Eschericia coli* Y1090 (ΔlacU169, proA+, Δlon, araD139, supF, trpC22::tn10 [pMC9] ATCC#37197) in soft agar and incubated for 2, 5 hours at 42° C.

The plates were overlaid with sheets of Isopropyl-β-D-thiog-alacto pyranoside saturated sheets of nitrocellulose and incubation was continued for 2, 5 hours at 37° C. The nitrocellulose was removed and incubated with samples of the monoclonal antibodies in PBS with Tween 20 added to a final concentration of 0.05%. Bound monoclonal antibodies were visualized by horseradish peroxidase-conjugated rabbit antimouse immunoglobulins (P260, Dako, Glostrup, DK) and a staining reaction involving 5,5', 3,31 tetramethyl benzidine and $H_2O_2$.

Positive plaques were recloned and the phages originating from a single plaque were used to lysogenize *E. coli* Y1089 (ΔlacU169, proA+, Δlon, araD139, strA, hfl150 [chr::tn10] [pMC9] ATCC nr. 37196). The resultant lysogenic strains were used to propagate phage particles for DNA extraction. These lysogenic *E. coli* strains have been deposited in the German Collection of Microorganisms and Cell Cultures in Braunschweig, FRG under the DSM-Accession numbers:

DSM 8377=AA226 (expressing ST-3 reactive polypeptide),

DSM 8378=AA227 (expressing HYB76-8 reactive polypeptide),

DSM 8379=AA242 (expressing PV-2 reactive polypeptide).

A physical map of the recombinant phages is shown in FIG. 8 and the expression of the recombinant gene products is shown FIG. 9.

The HYB76-8 and ST-3 binding proteins are expressed as fusion proteins fused to β-galactosidase whereas the PV-2 binding protein appear to be expressed in an unfused version.

Sequencing of the nucleotide sequence encoding the HYB76-8 binding protein. In order to obtain the nucleotide sequence of the gene encoding the HYB76-8 binding protein the 1.7 kbp *M. tuberculosis* derived EcoRI—BamHI fragment from AA227 was subcloned in pBluescriptSK+ (Stratagene, La Jolla, Calif.) (FIG. 10A) and used to transform *E. coli* XL-1Blue (Stratagene, La Jolla, Calif.).

The complete DNA sequence obtained by the dideoxy sequencing method (Sanger, F. et al. 1977, 'DNA sequencing with chain terminating inhibitors'. Proc. Natl. Acad. Sci. 74: 5463) and cycle sequencing using the Dye Terminator system in combination with the automated gel reader, model 373A from Applied Biosystems, is shown in FIG. 10B. An open reading frame encoding a sequence of 95 amino acid residues was identified from an ATG start codon at position 13–15 extending to a TAG stop codon at position 298–300.

The deduced amino acid sequence is shown in FIG. 10C using conventional three letter code. The * indicate amino acids which could be aligned to the sequence obtained after N-terminal sequencing of biochemically purified native material.

Comparison of deduced and observed amino acid composition of ESAT6 The aminoacids are compared to Leucine which was assigned the value = 1

|  | observed | deduced from DNA sequence |
|---|---|---|
| Asp + Asn: | 1.05 | 1.16 |
| Thr: | 0.98 | 1.1 |
| Ser: | 1.00 | 1.1 |
| Glu + Gln: | 2.57 | 2.3 |
| Pro: | 0.02 | 0.14 |
| Gly: | 1.43 | 1.4 |
| Ala: | 2.22 | 2.4 |
| Val: | 0.43 | 0.6 |
| Met: | 0.06 | 0.43 |
| Ile: | 0.53 | 0.6 |
| Leu: | 1.00 | 1.00 |
| Phe: | 0.26 | 0.3 |
| His: | 0.16 | 0.14 |
| Lys: | 0.38 | 0.43 |
| Arg: | 0.14 | 0.14 |
| Cys: | 0.14 | 0 |

No homologous sequences were found by searching the GenEMBL databases using the Sequence Analysis Software Package version 7.1 from the Genetics Computer Group associated with the University of Wisconsin (Devereux, J. et al. 1984). The HYB76-8 binding protein is therefore believed to be novel.

Example 5

Immunodominance of the low molecular weight secreted antigens

The stimulatory potential of secreted protein fractions was investigated in outbred guinea pigs and human donors. This was done to analyze the possible influence of genotype and experimental design on the relative immunodominance of the 6–10 kDa secreted antigen fraction.

T cell responses in different strains of inbreed mice. Genetically different strains of inbreed mice representing different MHC kl 2 haplotypes were infected with *M. tuberculosis* for 14 days. Splenic T cells were isolated and stimulated with the panel of secreted protein fractions (FIG. 11). The release of IFN-γ in the cultures were quantified and the response pattern of the different strains compared (FIG. 13).

Five out of six strains of mice demonstrated a predominant recognition of fraction 1 a result which further supported the notion that this fraction is generally immune-dominant during the live infection.

Stimulatory capacity of ST-CF fractions in sensitized guinea pigs. Groups of outbred guinea pigs from strains Ssc:AL were sensitized by infection with *M. tuberculosis*, BCG i.d., BCG i.v., or immunized with killed *M. tuberculosis* in oil or (as a control) with oil alone. *M. tuberculosis* H37Rv and *M. bovis* BCG Copenhagen were used.

When infected with *M. tuberculosis* H37Rv guinea pigs were given $2.5 \times 10^3$ cfu in a volume of 0.1 ml in an ear vein. Infection by the same route (i.v.) with BCG was done with $2.5 \times 10^4$ cfu. Vaccinations with BCG were done with four intradermal (i.d.) injections on the abdomen of 0.1 ml reconstituted BCG vaccine. BCG Copenhagen contained approximately $4 \times 10^6$ cfu per ml of the reconstituted preparation. Immunizations with killed bacteria were given $4 \times 0.1$ ml i.d. on the abdomen of a suspension of glutaraldehyde killed bacteria at 0.4 mg (semidry weight) per ml of paraffine oil (Marcol 52 (M52)).

3–4 weeks later peripheral blood and spleen lymphocytes were isolated and used for stimulation experiments with a set of 10 fractions of ST-CF (prepared as in: Andersen & Heron, 1993a). The MW of these fraction appears from FIG. 11.

Peripheral blood lymphocytes were isolated from blood drawn by cardiac puncture using EDTA as anticoagulant. Erythrocytes were removed by ficoll density gradient (d=1.09) centrifugation. Lymphocytes were washed twice, counted and the cell concentration adjusted to $2 \times 10^6$ cells/ml in RPMI 1640 with supplements including 5% FCS. Spleen lymphocytes were isolated by pressing spleens through a wire mesh. Erythrocytes were lysed by treatment with 0.84% $NH_4Cl$. The lymphocytes were washed twice and the cell concentration adjusted to $2 \times 10^6$ cells/ml of RPMI with supplements.

0.1 ml of cells were cultured with 0.1 ml of antigen or mitogen in triplicate for 6 days, the last 22 h in the presence of 1 μCi $^3$H-thymidine. Cultures were harvested and incorporated $^3$H-thymidine was counted in a scintillation counter. Results are calculated as geometric means of triplicate cultures, and geometric means between guinea pigs within immunization groups are shown in FIGS. 12A and 12B.

There was no significant stimulation of PBL or SPL from control (M52, oil alone) immunized guinea pigs. For both cell types it is evident that infection with *M. tuberculosis* or BCG leads to a highly significant superior sensitivity to fraction 1 than to the other fractions. With the exception of peripheral blood lymphocytes from the BCG i.d. group which showed a peak for fractions 5–7 and 10, there was no noteworthy differences between responses to fraction 2–10 in the infected animals. When immunizing with killed *M. tuberculosis*, peak responses to fraction 1, 7, and 10 were seen for both cell types. It should be noted that this group is the only one in which fraction 1 does not give a significantly higher response than all other fractions, thereby supporting the general conclusion that responses to the low molecular mass secreted antigens is associated with the live infection. These results underline the importance of the <10000 Da region in the response to infection with *M. tuberculosis* "complex" mycobacteria.

IFN-γ release in human lymphocyte cultures stimulated with ST-CF fraction. Peripheral blood mononuclear cells (PBMC) were obtained from heparinized venous blood from human donors, diluted 1:1 in saline, and separated by sedimentation over Lymphoprep (Nycomed A/S, Oslo, Norway) density gradient centrifugation. Cells were collected, washed twice and cultured in flat-bottomed microtiter plates (Nunc, Roskilde, Denmark), at $5 \times 10^4$ cells per well, in a volume of 200 μg of RPMI 1640 containing 10%. human AB serum and ST-CF fractions (1–2 μg/ml.). Supernatants were harvested from the lymphocyte cultures at day 5. The amount of IFN-γ present was quantified by an IFN-γ enzyme-linked immunosorbent assay kit (Holland Biotechnology, Leiden, The Netherlands).

Patients with newly diagnosed active Tb were found to be characterized by a marked production of IFN-γ to a range of ST-CF fractions. This is in contrast to the other donor groups (BCG vaccinated and patients with advanced disease) which demonstrated a rather limited reactivity to secreted protein fractions (FIG. 14).

Secreted proteins of molecular mass 6–10 kDa were found to posses a superior IFN-γ inducing capability in the active Tb patients and elicited a mean release of 35 u/ml (6125 pg/ml).

Conclusions. ST-CF is a mixture of antigens secreted by *M. tuberculosis* during growth. ST-CF is herein demonstrated to contain protective antigens which can be administered as an experimental vaccine and evoke the same level of specific acquired resistance as live BCG. The immunodominant T-cell antigen in this complex mixture has been identified in three different models.

Human patients with newly diagnosed tuberculosis as well as guinea pigs and mice infected with a virulent strain of *M. tuberculosis* respond powerfully to secreted antigens and the most potent fraction containing proteins ranging from 6–10 kDa.

In long-term memory immune mice it is demonstrated that one of the major targets for memory effector T-cells triggered during the first phase of a protective immune response is the same low molecular mass fraction. A protein band within this fraction responsible for the pronounced reactivity has been identified as a 6 kDa protein antigen defined by the mAb HYB76-8. A procedure has been devised for the purification of this protein and the gene encoding the protein has been cloned and sequenced.

Both biochemically purified and recombinant HYB76-8 reactive antigen were demonstrated to posses the powerful IFN-γ inducing capacity. A vaccine based on a chemically purified protein fraction highly enriched in the 6 kDa antigen induced substantial levels of protection whereas vaccines based on purified recombinant HYB76-8 reactive antigen provoked predominantly TH-2 responses of low protective efficacy. Experiments are in progress to optimize the adjuvant used, thereby allowing the monitoring of the protective efficacy of purified proteins too.

Example 6

ESAT6 as a diagnostic agent in a skin test.

In order to test the possible use of ESAT6 as a diagnostic agent, the following experiment was carried out:

Four groups of guinea pigs (n=5) were exposed to aerosols of *M. tuberculosis* Erdman at doses giving rise to an average of 5 primary tuberculous lesions per lung. Skin testings were performed after 3, 6, 8, and 11 weeks after inhalation with 1 μg of purified ESAT6.

As can be seen from FIG. 15 a positive skin test reaction (>5 mm) was observed in all guinea pigs 11 weeks after infection. A clear division in a responding and a non-responding group was observed at earlier time points.

Example 7

Species distribution of ESAT-6 in culture filtrate from various mycobacteria species and of esat-6 on chromosomal DNA from various mycobacteria.

In order to examine the species distribution of ESAT-6, a panel of culture filtrates (produced as described herein) were analyzed by Western blotting using HYB 76-8 as the probe (Sorensen et al. 1995). Furthermore, in order to determine the distribution of the esat-6 gene within species belonging to the tuberculosis complex and other mycobacteria, PCR analyses were used as described by Oettinger and Andersen (Oettinger, T. and Andersen, A. B., 1994. Cloning and B-cell Epitope Mapping of MPT64 from *Mycobacterium tuberculosis* H37Rv. Infect. Immun. 62: 2058–2064). The primers used for the PCR are shown in Table 4.

TABLE 4

Sequence of the esat-6 oligonucloetides

| Orientation and digonucloetide | Sequence (5'–3') | Position (nt) in SEQ ID NO. 1 |
|---|---|---|
| Sense | | |
| esat.16 | CAA GCT CGC AGC GGC CTG GG | 123–142 |
| esat.17 | CAT GAC AGA GCA GCA GTG | 12–29 |
| Antisense | | |
| esat.15 | GTT GTT CAG CTC GGT AGC CG | 213–194 |
| esat.18 | GCC CTA TGC GAA CAT CCC | 303–286 |

The results of the Western blotting and the PCR experiments are shown in table 5.

TABLE 5

Interspecies analyses for ESAT-6 and esat-6

| Strain | esat.17 + esat.18 | esat.15 + esat.16 | esat.16 + esat.18 | esat.17 + esat15 | Western blotting |
|---|---|---|---|---|---|
| *M. tuberculosis* H37Rv | + | + | + | + | + |
| *M. tuberculosis* H37Ra | + | + | + | + | ND |
| *M. tuberculosis* Erdman | + | + | + | + | + |
| *M. bovis* BCG Danish 1331 | − | − | − | − | − |
| *M. bovis* BCG Tokyo | − | − | − | − | − |
| *M. bovis* BCG Glaxo | − | − | − | − | − |
| *M. bovis* BCG Pasteur | − | − | − | − | − |
| *M. bovis* BCG Tice | − | − | − | − | − |
| *M. bovis* BCG Moreau | − | − | − | − | − |
| *M. bovis* BCG Russian | − | − | − | − | − |
| *M. bovis* MWC 27 | + | + | + | + | ND |
| *M. africanum* | + | + | + | + | + |
| *M. leprae* | − | − | − | − | ND |
| *M. avium* | − | − | − | − | − |
| *M. kansasii* | + | + | + | + | + |
| *M. marinum* | − | − | − | − | + |
| *M. scrofulaceum* | − | − | − | − | − |
| *M. intercellulare* | − | − | − | − | − |
| *M. fortuitum* | − | − | − | − | − |
| *M. xenopi* | − | − | − | − | − |
| *M. flaveum* | + | − | − | − | ND |
| *M. szulgai* | − | − | − | − | + |
| *E. coli* | − | − | − | − | ND |
| *S. aureus* | − | − | − | − | ND |

+: Positive reaction; −: No reaction; ND: Not determined

From table 5 it is concluded that the expression of ESAT-6 is confined to *M. tuberculosis* complex strains, to *M. kansasii*, to *M. marinum*, and to *M. szulgai*. None of the *M. bovis* BCG vaccine substrains express the ESAT-6 antigen. The PCR analyses confirm and extend the Western blot analyses concerning the *M. tuberculosis* complex and *M. kansasii*. However, the method did not demonstrate the presence of the esat-6 gene on chromosomal DNA from *M. marinum* and *M. szulgai*.

Furthermore, PCR on chromosomal DNA from 10 *M. tuberculosis* strains isolated from Danish tuberculosis patients and strains isolated from 10 Tanzanian tuberculosis patients all demonstrated the presence of the esat-6 gene (data not shown). This finding demonstrates that the esat-6 gene is conserved among clinical isolates of *M. tuberculosis*.

REFERENCES

Andersen, P., D. Askgaard, L. Ljungqvist, J. Bennedsen, I. Heron. 1991a, T-cell proliferative response to antigens secreted by *Mycobacterium tuberculosis*. Infection and Immunity 59: 1558–1563.

Andersen, P., D. Askgaard, L. Ljungqvist, J. Bennedsen, I. Heron. 1991b. Proteins released from *Mycobacterium tuberculosis* during growth. Infection and Immunity. 59: 1905–1910.

Andersen, P., and I. Heron. 1993a. Specificity of a Protective Memory Immune Response against *Mycobacterium tuberculosis*. Infection and Immunity. 61: 844–851.

Andersen, P., and I. Heron. 1993b. Simultaneous electroelution of whole SDS-polyacrylamide gels for the direct cellular analysis of complex protein mixtures. J. Immunol. Methods 161: 29–39.

Chang et al. 1978. Nature, 375: 515.

Crea et al. 1978. Proceeding of the National Academy of Sciences USA, 75: 5765.

Devereux, J., P. Haeberli, and O. Smithies. 1984. A comprehensive set of sequence analysis programs for the VAX. Nucleic Acids. Res. 12: 387–395.

Fiers et al. 1978. Nature, 273: 113.

Flesch, I., and S.H.E. Kaufmann. 1987. Mycobacterial growth inhibition by interferon-gamma-activated bone marrow macrophages and differential susceptibility among strains of *M. tuberculosis*. J. Immunol. 138: 4408–4413.

Goeddel et al. 1979. Nature, 281: 544.

Hess et al. 1968. Journal of Advanced Enzyme Regulation, 7: 149.

Hitzeman et al. 1980. Journal of Biological Chemistry, 255: 2073.

Holland et al. 1978. Biochemistry, 17: 4900.

Itakura et al. 1977. Science, 198: 1056.

Jones. 1977. Genetics, 84: 12.

Lefford, M. J., and D. D. McGregor. 1974. Immunological memory in tuberculosis. Cell. Immunol. 14: 417–428.

Messing et al. 1981. Third Cleveland Symposium on Macromolecules and Recombinant DNA, Ed. A Walton, Elsevier, Amsterdam.

Oettinger, T. and Andersen, A. B., 1994. Cloning and B-cell Epitope Mapping of MPT64 from *Mycobacterium tuberculosis* H37Rv. Infect. Immun. 62: 2058–2064.

Orme, I. M. 1988. Characteristics and specificity of acquired immunologic memory to *M. tuberculosis* infection. J. Immunol. 140: 3589–3593.

Rook, G.A.W. 1990. The role of activated macrophages in protection and immunopathology in tuberculosis. Res. Microbiol. 141: 253–256.

Sambrook J, Fritsch EF, Maniatis T. 1989. Molecular cloning: a laboratory manual, 2nd ed. Cold Spring Harbor Laboratory, Cold Spring Harbor, N.Y.

Sanger, F., S. Nickles, and A. R. Coulson. 1977. DNA sequencing with chainterminating inhibitors. Proc. Natl. Acad. Sci. 74: 5463.

Siebwenlist et al. 1980. Cell, 20: 269.

Stinchomb et al. 1979. Nature 282: 39.

Tschemper et al. 1980. Gene, 10: 157.

Ulmer JB et al. 1993. Curr. Opin. Invest. Drugs, 2: 983–989.

Young, R. A., B. R. Bloom, C. M. Grosskinsky, J. Ivanyi, D. Thomas, and R. W. Davis. 1985. Dissection of *Mycobacterium tuberculosis* antigens using recombinant DNA. Proc. Natl. Acad. Sci. USA 82: 2583–2587.

---

We claim:

1. A polypeptide which is
   (a) a polypeptide which is purified, and which is released from metabolizing mycobacteria belonging to the tuberculosis complex and can be isolated from filtrates from such mycobacteria grown as shaken cultures for 7 days, and has a molecular weight in the range from about 3 kDa to about 16 kDa, the molecular weight being determined by analysis by SDS-PAGE and silver staining, or
   (b) a non-naturally occurring polypeptide which comprises a subsequence of the polypeptide of (a) above, which subsequence comprises a T cell epitope of the polypeptide of (a) above,
   which polypeptide of (a) or (b) induces a release of IFN-γ (interferon-γ) of at least 1500 pg/ml from reactivated memory T-lymphocytes withdrawn from a C57Bl/6j mouse within 4 days after the mouse has been rechallenge infected with mycobacteria belonging to the tuberculosis complex, the induction performed by the addition of the polypeptide of (a) or (b) to a suspension comprising about 200,000 reactivated memory T-cells per ml, the addition of the polypeptide of (a) or (b) resulting in a concentration of 1 μg per ml suspension, the release of IFN-γ being assessable by determination of IFN-γ in supernatant harvested 2 days after the addition of the polypeptide of (a) or (b) to the suspension,
   said polypeptide of (a) or (b) having the ability of eliciting a delayed type hypersensitivity reaction.

2. A polypeptide of (a) or (b) according to claim 1, wherein the polypeptide has a molecular weight in the range of about 4 to about 14 kDa.

3. A polypeptide of (a) or (b) according to claim 1, wherein the polypeptide is selected from the group consisting of a *Mycobacterium tuberculosis* derived polypeptide which is produced by the lysogenic *E. coli* strain designated AA227 which has been deposited Jun. 28, 1993 with the collection of Deutche Sammlung von Mikroorganismen und Zellkulturen GmbH (DSM) under the accession number DSM 8378 in accordance with the provisions of the Budapest Treaty, a *Mycobacterium tuberculosis* derived polypeptide which is produced by the lysogenic *E. coli* strain designated AA242 which has been deposited Jun. 28, 1993 with the collection of Deutsche Sammlung von Mikroorganismen under Zellkultruen GbhH (DSM) under the accession number DSM 8379 in accordance with the provisions of the Budapest Treaty, and a *Mycobacterium tuberculosis* derived polypeptide which reacts in a western blot assay with a monoclonal antibody, HYB76-8, said antibody being produced by the hybridoma cell line designated HYB 76-8 0,5/br C8 0,25/br B3 which has been deposited Jun. 30, 1993 with the collection of Deutsche Sammlung von Mikroorganismen und Zellkulturen GmbH (DSM) under the accession number DSM ACC2134 in accordance with the provisions of the Budapest Treaty.

4. A polypeptide of (a) or (b) according to claim 1, wherein the polypeptide is encodable by a nucleic acid fragment, which fragment (1) specifically hybridizes, under stringent hybridization conditions, with a probe consisting of the nucleotide sequence shown in SEQ ID NO: 1 or consisting of an effective subsequence thereof encoding a T-cell epitope, or with a probe complementary to the entire length of the nucleotide sequence shown in SEQ ID NO: 1 or complementary to an effective subsequence of SEO ID NO: 1 encoding a T-cell epitope.

5. A composition comprising a plypeptide of (a) or (b) according to claim 1, further comprising an adjuvant.

6. A polypeptide of (a) or (b) according to claim 1, wherein the IFN-γ released from the memory T-lymphocytes is at least 2000 pg/ml.

7. A composition comprising a polypeptide of (a) or (b) according to claim 1, further comprising any other polypeptide derived from a bacterium belonging to the tuberculosis complex.

8. A composition comprising at least two different polypeptides, each polypeptide being as defined in claim 1.

9. A composition according to claim 8, comprising 3–20 different polypeptides, each polypeptide being as defined in claim 1.

10. A composition comprising as the effective component a microorganism, wherein at least one copy of a DNA fragment comprising a DNA sequence encoding a polypeptide of (a) or (b) as defined in claim 1 has been incorporated into the genome of the microorganism in a manner allowing the microorganism to express the polypeptide.

11. A composition according to claim 10, wherein the microorganism is a bacterium.

12. A composition according to claim 11, wherein the bacterium is selected from the group consisting of the genera Mycobacterium, Salmonella, Pseudomonas and Eschericia.

13. A composition according to claim 12, wherein the microorganism is *Mycobacterium bovis* BCG.

14. A composition according to claim 10, wherein at least 2 copies of a DNA fragment encoding a polypeptide of (a) or (b) as defined in claim 1 are incorporated into the genome of the microorganism.

15. A composition according to claim 14 wherein the number of copies is at least 5.

16. A composition according to claim 10, wherein the DNA fragment which has been incorporated in the microorganism 1) specifically hybridizes, under stringent hybridization conditions, with a probe consisting of the nucleotide sequence shown in SEQ ID NO: 1 or consisting of an effective subsequence thereof encoding a T-cell epitope, or with a probe perfectly complementary to the entire length of the nucleotide sequence shown in SEO ID NO: 1 or perfectly complementary to the entire length of an effective subsequence of SEO ID NO: 1 encoding a T-cell epitope, said probe being, in any of the above cases, or a length equal to or greater than said nucleic acid fragment encoding said polypeptide.

17. A composition according to claim 16 wherein the DNA-sequence encodes the polypeptide with the amino acid sequence shown in SEQ ID NO: 2, or encodes a subsequence thereof.

18. A composition comprising a polypeptide of (a) or (b) according to claim 1, which further comprises dimethyldiocadecylammonium bromide (DDA).

19. A polypeptide of (a) or (b) according to claim 1, wherein the polypeptide has a molecular weight in the range of about 6 to 10 kDa.

20. A polypeptide of (a) or (b) according to claim 1, wherein the polypeptide has a molecular weight in a range of about 6–8 kDa.

21. A polypeptide of (a) or (b) according to claim 1, wherein the IFN-γ released from the memory T-lymphocytes is at least 3000 pg/ml.

22. A composition according to claim 7, wherein the any other polypeptide is selected from the group consisting of the ST-3 reactive polypeptide, the PV-2 reactive polypeptide, MPB64, MPT64, and MPB59.

23. The polypeptide of (a) or (b) of claim 1 wherein the polypeptide is a non-naturally occurring polypeptide which is a peptide of at least 12 amino acids.

24. The polypeptide of (a) or (b) of claim 1 wherein said polypeptide is a polypeptide having the amino acid sequence of SEQ ID NO: 2.

25. The polypeptide of (a) or (b) of claim 1 wherein said polypeptide is a non-naturally occurring polypeptide comprising a T cell epitope of the polypeptide having the amino acid sequence of SEQ ID NO: 2.

26. The polypeptide of (a) or (b) of claim 1 wherein said polypeptide is a non-naturally occurring polypeptide comprising at least a 12 amino acid subsequence of the amino acid sequence of SEQ ID NO: 2.

27. A purified or non-naturally occurring polypeptide which comprises a T cell epitope of a polypeptide having the amino acid sequence of SEQ ID NO: 2, which polypeptide induces a release of IFN-$\gamma$ (interferon-$\gamma$) of at least 1500 pg/ml from reactivated memory T-lymphocytes withdrawn from a C57Bl/6j mouse within 4 days after the mouse has been rechallenge infected with mycobacteria belonging to the tuberculosis complex, the induction performed by the addition of the polypeptide to a suspension comprising about 200,000 reactivated memory T-cells per ml, the addition of the polypeptide resulting in a concentration of 1 $\mu$g per ml suspension, the release of IFN-$\gamma$ being assessable by determination of IFN-$\gamma$ in supernatant harvested 2 days after the addition of the polypeptide to the suspension, said polypeptide having the ability of eliciting a delayed type hypersensitivity reaction.

28. A purified or non-naturally occurring polypeptide which comprises the amino acid sequence of SEQ ID NO: 2.

29. A composition for diagnosing tuberculosis caused by mycobacteria belonging to the tuberculosis complex, comprising a polypeptide as defined in claim 27 in combination with a pharmaceutically acceptable carrier or vehicle.

30. The polypeptide of claim 1 which is not BCG-a or a fragment thereof which comprises a T-cell epitope of BCG-a.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 1756 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 13..297

(xi) SEQUENCE DESCRIPTION: SEQ ID NO: 1:

```
GAATTCCAAA AC ATG ACA GAG CAG CAG TGG AAT TTC GCG GGT ATC GAG          48
              Met Thr Glu Gln Gln Trp Asn Phe Ala Gly Ile Glu
                1               5                  10

GCC GCG GCA AGC GCA ATC CAG GGA AAT GTC ACG TCC ATT CAT TCC CTC        96
Ala Ala Ala Ser Ala Ile Gln Gly Asn Val Thr Ser Ile His Ser Leu
         15                  20                  25

CTT GAC GAG GGG AAG CAG TCC CTG ACC AAG CTC GCA GCG GCC TGG GGC       144
Leu Asp Glu Gly Lys Gln Ser Leu Thr Lys Leu Ala Ala Ala Trp Gly
     30                  35                  40

GGT AGC GGT TCG GAG GCG TAC CAG GGT GTC CAG CAA AAA TGG GAC GCC       192
Gly Ser Gly Ser Glu Ala Tyr Gln Gly Val Gln Gln Lys Trp Asp Ala
 45                  50                  55                  60

ACG GCT ACC GAG CTG AAC AAC GCG CTG CAG AAC CTG GCG CGG ACG ATC       240
Thr Ala Thr Glu Leu Asn Asn Ala Leu Gln Asn Leu Ala Arg Thr Ile
                 65                  70                  75

AGC GAA GCC GGT CAG GCA ATG GCT TCG ACC GAA GGC AAC GTC ACT GGG       288
Ser Glu Ala Gly Gln Ala Met Ala Ser Thr Glu Gly Asn Val Thr Gly
         80                  85                  90

ATG TTC GCA TAGGGCAACG CCGAGTTCGC GTAGAATAGC GAAACACGGG               337
Met Phe Ala
         95

ATCGGGCGAG TTCGACCTTC CGTCGGTCTC GCCCTTTCTC GTGTTTATAC GTTTGAGCGC     397
```

```
ACTCTGAGAG GTTGTCATGG CGGCCGACTA CGACAAGCTC TTCCGGCCGC ACGAAGGTAT    457

GGAAGCTCCG GACGATATGG CAGCGCACGC GTTCTTCGAC CCCAGTGCTT CGTTTCCGCC    517

GGCGCCCGCA TCGGCAAACC TACCGAAGCC AACGGCCAG ACTCCGCCCC CGACGTCCGA     577

CGACCTGTCG GAGCGGTTCG TGTCGGCCCC GGCCGCCACC CCCCCACCCC CACCTCCGCC    637

TCCGCCAACT CCGATGCGAT CGCGCAGGAG AGCCGCCCTC GCCGGAACCG GCCGCATCTA    697

AACCACCCAC ACCCCCCATG CCCATCGCCG GACCCGAACC GGCCCCACCC AAACCACCCA    757

CACCCCCCAT GCCCATCGCC GGACCCGAAC CGGCCCCACC CAAACCACCC ACACTCCGAT    817

GCCCATCGCC GGACCTGCAC CCCACCCAAC GAATCCCAGT TGGCGCCCCC CAGACCACCG    877

ACACCACAAA CGCCAACCGG AGCGCCGCAG CAACGGAAT CACCGGTGCC CCACGTACCC     937

TCGCACGGGC CACATCAACC CCGGTGCACC GCACCAGCAC CGCCCTGGGC AAAGATGCCA    997

ATCGGCGAAC CCCCGCCCGC CGTCCAGAC CGTCTGCGTC CCCGGCCGAA CCACCGACCC    1057

GGCCTGCCCC CCAACACTCC CGACGTGCGC GCCGGGTCA CCGCTATCGC ACAGACACCG    1117

AACGAAACGT CGGGAAGGTA GCAACTGGTC CATCCATCCA GGCGCGGCTG CGGGCAGAGG   1177

AAGCATCCGG CGCGCAGCTC GCCCCCGGAA CGGAGCCCTC GCCAGCGCCG TTGGGCCAAC   1237

CGAGATCGTA TCTGGCTCCG CCCACCCGCC CCGCGCCGAC AGAACCTCCC CCCAGCCCCT   1297

CGCCGCAGCG CAACTCCGGT CGGCGTGCCG AGCGACGCGT CCACCCCGAT TTAGCCGCCC   1357

AACATGCCGC GGCGCAACCT GATTCAATTA CGGCCGCAAC CACTGGCGGT CGTCGCCGCA   1417

AGCGTGCAGC GCCGGATCTC GACGSGRMAA CAGAAATCCT TAAGCCGGCG CGAAGGGGCC   1477

GCAAGGTGAA GAAGGTGAAG CCCCAGAAAC CGAAGGCCAC GAAGCCGCCC AAAGTGGTGT   1537

CGCAGCGCGG CTGGCGACAT TGGGTGCATG CGTTGACGCG AATCAACCTG GCCTGTCAC    1597

CCGACGAGAA GTACGAGCTG GACCTGCACG CTCGAGTCCG CCGCAATCCC CGCGGGTCGT   1657

ATCAGATCGC CGTCGTCGGT CTCAAAGGTG GGCTGGCAA AACCACGCTG ACAGCAGCGT    1717

TGGGGTCGAC GTTGGCTCAG GTGCGGGCCG ACCGGATCC                          1756
```

(2) INFORMATION FOR SEQ ID NO: 2:

(i) SEQUENCE CHARACTERISTICS:
        (A) LENGTH: 95 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Thr Glu Gln Gln Trp Asn Phe Ala Gly Ile Glu Ala Ala Ser
 1               5                  10                  15

Ala Ile Gln Gly Asn Val Thr Ser Ile His Ser Leu Leu Asp Glu Gly
                20                  25                  30

Lys Gln Ser Leu Thr Lys Leu Ala Ala Ala Trp Gly Gly Ser Gly Ser
            35                  40                  45

Glu Ala Tyr Gln Gly Val Gln Gln Lys Trp Asp Ala Thr Ala Thr Glu
        50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
            85                  90                  95
```